(12) United States Patent
Van Malderen et al.

(10) Patent No.: US 12,357,515 B2
(45) Date of Patent: Jul. 15, 2025

(54) ABSORBENT ARTICLE WITH SPACER ELEMENT

(71) Applicant: Drylock Technologies NV, Zele (BE)

(72) Inventors: Bart Van Malderen, Zele (BE); Steven Smet, Zele (BE); Werner Van Ingelgem, Zele (BE)

(73) Assignee: Drylock Technologies NV, Zele (BE)

( * ) Notice: Subject to any disclaimer, the term of this patent is extended or adjusted under 35 U.S.C. 154(b) by 863 days.

(21) Appl. No.: 17/250,037

(22) PCT Filed: May 14, 2019

(86) PCT No.: PCT/EP2019/062301
§ 371 (c)(1),
(2) Date: Nov. 10, 2020

(87) PCT Pub. No.: WO2019/219655
PCT Pub. Date: Nov. 21, 2019

(65) Prior Publication Data
US 2021/0161731 A1  Jun. 3, 2021

(30) Foreign Application Priority Data
May 14, 2018  (EP) ..................................... 18172153

(51) Int. Cl.
*A61F 13/515* (2006.01)
*A61F 13/51* (2006.01)
(Continued)

(52) U.S. Cl.
CPC .......... *A61F 13/515* (2013.01); *A61F 13/534* (2013.01); *A61F 2013/51019* (2013.01);
(Continued)

(58) Field of Classification Search
CPC .................. A61F 13/515; A61F 13/534; A61F 2013/51019; A61F 2013/51021;
(Continued)

(56) References Cited

U.S. PATENT DOCUMENTS 3,595,235 A * 7/1971 Jespersen .......... A61F 13/01008
526/204
3,612,054 A * 10/1971 Matsuda ........... A61F 13/53713
604/377
(Continued)

FOREIGN PATENT DOCUMENTS

EP    0360285 A2 *  3/1990
EP    2627294 A1     8/2013
(Continued)

OTHER PUBLICATIONS

"International Application Serial No. PCT/EP2019/062301, International Search Report mailed Sep. 18, 2019", (Aug. 19, 2019), 4 pgs.
(Continued)

*Primary Examiner* — Adam Marcetich
*Assistant Examiner* — Ted Yang
(74) *Attorney, Agent, or Firm* — Schwegman Lundberg & Woessner, P.A.

(57) ABSTRACT

An absorbent article having a front edge intended to be positioned at a front side of a person and a rear edge intended to be positioned at a rear side of a person, said absorbent article comprising a liquid pervious topsheet, a liquid impervious backsheet, and an absorbent material between said topsheet and said backsheet, wherein at least a first spacer element is included between said topsheet and said backsheet, wherein the first spacer element has a top side facing the topsheet, a bottom side facing the backsheet, and a number of lateral sides between the top and the bottom side,
(Continued)

and wherein the absorbent material extends along at least two opposite lateral sides of the first spacer element; said first spacer element being configured to guide liquid to the absorbent material upon wetting of the absorbent article.

20 Claims, 8 Drawing Sheets

(51) Int. Cl.
A61F 13/53 (2006.01)
A61F 13/534 (2006.01)
(52) U.S. Cl.
CPC .............. A61F 2013/51021 (2013.01); A61F 2013/530007 (2013.01); A61F 2013/530481 (2013.01); A61F 2013/530868 (2013.01); A61F 2013/5349 (2013.01)
(58) Field of Classification Search
CPC ........ A61F 2013/530007; A61F 2013/530481; A61F 2013/530868; A61F 2013/5349; A61F 13/53756; A61F 13/5323; A61F 13/535; A61F 13/537; A61F 13/53747; A61F 2013/530262; A61F 2013/530437; A61F 13/53752; A61F 2013/53765; A61F 2013/53089; A61F 13/531; A61F 13/53708; A61F 13/53717; A61F 2013/53795; A61F 2013/53769; A61F 13/53743; A61F 2013/530927; A61F 2013/530956; A61F 13/532
See application file for complete search history.

(56) References Cited

U.S. PATENT DOCUMENTS

| | | | | |
|---|---|---|---|---|
| 4,670,011 A * | 6/1987 | Mesek | .............. | A61F 13/15634 604/378 |
| 4,678,464 A * | 7/1987 | Holtman | ............... | A61F 13/533 604/385.03 |
| 4,960,477 A * | 10/1990 | Mesek | ................ | A61F 13/5323 D24/126 |
| 5,185,009 A * | 2/1993 | Sitnam | .............. | A61F 13/15252 604/367 |
| 5,342,337 A * | 8/1994 | Runeman | .............. | A61F 13/535 604/385.19 |
| 5,514,120 A * | 5/1996 | Johnston | ........... | A61F 13/53752 604/385.101 |
| 5,613,962 A * | 3/1997 | Kenmochi | ........ | A61F 13/53717 604/382 |
| 5,895,379 A * | 4/1999 | Litchholt | .......... | A61F 13/53752 604/378 |
| 2004/0078020 A1 * | 4/2004 | Kawata | ................... | A61F 13/82 604/385.101 |
| 2006/0081348 A1 * | 4/2006 | Graef | .................. | A61F 13/5376 604/385.01 |
| 2013/0143020 A1 * | 6/2013 | Wood | .................... | A61F 13/537 428/220 |
| 2013/0211358 A1 * | 8/2013 | Kikkawa | ............... | A61F 13/534 604/367 |
| 2015/0038929 A1 * | 2/2015 | Van Malderen | ...... | A61F 13/515 604/385.01 |
| 2015/0065973 A1 * | 3/2015 | Roe | ........................ | A61F 13/533 604/374 |
| 2015/0065976 A1 * | 3/2015 | Roe | ......................... | A61F 13/42 604/374 |
| 2015/0209200 A1 * | 7/2015 | Fouillet | ................. | A61F 13/535 604/378 |
| 2015/0313771 A1 * | 11/2015 | Bergstrom | ............ | A61F 13/539 604/385.101 |
| 2015/0320615 A1 * | 11/2015 | Bergstrom | ............ | A61F 13/538 604/378 |
| 2016/0058630 A1 * | 3/2016 | Roe | ................... | A61F 13/49001 604/385.101 |
| 2016/0136009 A1 * | 5/2016 | Weisman | ................ | A61F 13/53 604/367 |
| 2016/0136012 A1 * | 5/2016 | Peri | ................... | A61F 13/53752 604/374 |
| 2016/0136013 A1 * | 5/2016 | Peri | ....................... | B65D 85/62 604/385.101 |
| 2016/0206483 A1 * | 7/2016 | Nishikawa | ........ | A61F 13/49001 |
| 2016/0235596 A1 * | 8/2016 | Ehrnsperger | .......... | A61F 13/537 |
| 2016/0270982 A1 * | 9/2016 | Raycheck | ......... | A61F 13/55105 |
| 2016/0354260 A1 * | 12/2016 | Roe | ........................ | A61F 13/532 |
| 2017/0079858 A1 * | 3/2017 | Willhaus | ............... | A61F 13/532 |
| 2017/0312149 A1 * | 11/2017 | Bianchi | .................. | A61L 15/28 |
| 2018/0116880 A1 * | 5/2018 | Garcia | .................. | A61F 13/537 |
| 2018/0140477 A1 * | 5/2018 | Minoguchi | ........ | A61F 13/49061 |
| 2018/0271719 A1 * | 9/2018 | Yuan | ................... | A61F 13/4942 |
| 2019/0247246 A1 * | 8/2019 | Yamaguchi | ............. | A61F 13/84 |
| 2019/0307617 A1 * | 10/2019 | Joshi | ...................... | A61F 13/53 |
| 2020/0179187 A1 * | 6/2020 | Tagomori | ................ | A61F 13/53 |
| 2021/0093489 A1 * | 4/2021 | Manabe | ............ | A61F 13/53752 |

FOREIGN PATENT DOCUMENTS

| | | | | |
|---|---|---|---|---|
| EP | 3536294 | | 9/2019 | |
| WO | 9711659 | | 4/1997 | |
| WO | WO-9947095 A1 * | | 9/1999 | ....... A61F 13/15617 |
| WO | WO-2012052173 A1 | | 4/2012 | |
| WO | WO-2018210758 A1 * | | 11/2018 | ............. A61F 13/00 |

OTHER PUBLICATIONS

"International Application Serial No. PCT/EP2019/062301, Written Opinion mailed Sep. 18, 2019", (Sep. 18, 2019), 9 pgs.

* cited by examiner ent with channels of the prior art,
ABSORBENT ARTICLE WITH SPACER ELEMENT

PRIORITY APPLICATIONS

This application is a U.S. National Stage Filing under 35 U.S.C. § 371 from International Application No. PCT/EP2019/062301, filed on May 14, 2019, and published as WO2019/219655 on Nov. 21, 2019, which claims the benefit of priority to European Application No. 18172153.1, filed on May 14, 2018; the benefit of priority of each of which is hereby claimed herein, and which applications and publication are hereby incorporated herein by reference in their entirety.

TECHNICAL FIELD

The present invention pertains to the technical field of absorbent articles, more preferably disposable personal care articles such as diapers, baby pants, adult incontinent garments, and the like, and to absorbent structures for use in such absorbent articles.

BACKGROUND

Disposable absorbent articles have an absorbent structure for absorbing bodily exudates, a soft liquid-permeable top sheet on the wearer side and a liquid-impermeable back sheet on the garment side. The absorbent structure in between is normally made from a mixture of cellulose fibers or other fibrous substance and an absorbent polymer material. These fibrous substances make these absorbent articles typically quite fluffy and bulky.

In recent years there has been increasing demand for flexible, thinner, lightweight absorbent structures to resolve various problems of manufacturing, marketing, design, fit, wearing comfort, distribution, garbage disposal, material and energy consumption, transportation and storage costs and the like.

The most common method currently used to meet these demands in disposable absorbent articles is to reduce the amount of cellulose fibre or other support material within and to surround the absorbent structure and/or use larger amounts of absorbent polymer materials. Consequently such absorbent articles have a smaller proportion of hydrophilic cellulose fibres and/or a higher proportion of absorbent polymers materials. Some of these absorbent articles may be better at storing liquid, however they are not necessarily good at absorbing and distributing liquid when the absorbent article is actually being used.

In order to obtain good absorbency, distribution and retention within such absorbent structures it has been found to be important to at least partially immobilize the absorbent material Failing to provide sufficient structural integrity results in loss of functional performance characteristics such as coherence, absorption, distribution and/or retention and results in failures related but not limited to for instance leakages, high rewet values, etc.

EP 2 627 294 relates to a method and apparatus for forming a composite structure, preferably for use in an absorbent structure used within the personal hygiene industry, such as for instance feminine hygiene garments, baby diapers and pants and adult incontinence garments. Particulate materials are deposited and positioned in a desired pattern onto a moving carrier layer. The method allows accurate forming of a pattern of particulate material clusters at high production speed having improved attachment properties, with reduced raw material usage and relative low cost.

WO 2012/052173 relates to a method and apparatus for forming a composite structure, preferably for use in an absorbent structure used within the personal hygiene industry, such as for instance feminine hygiene garments, baby diapers and pants and adult incontinence garments. The method comprises depositing particulate material in a desired pattern onto a moving carrier layer and positioning it into a pocketing pattern. The method allows accurate forming of a pre-determined pattern of particulate material clusters at high production speed, with reduced raw material usage and relative low cost. As such method allows manufacturing of absorbent structures being substantially cellulose free and substantially glue free, considered technically, economically and environmentally friendly.

There is a need in the art for an improved thin, flexible, lightweight absorbent structure which is discreet, sustainable and/or relatively inexpensive taking in mind manufacturing, marketing, design, fit, comfort, distribution, packaging, disposal, material, energy and transportation costs while preserving the required fluid absorption, distribution, transport, coherence and retention properties.

SUMMARY

The object of embodiments of the invention is to provide an absorbent article of the type stated in the preamble, with reduced manufacturing cost, light weight, thin, and good liquid distribution and absorption capacities.

According to a first aspect of the invention, there is provided an absorbent article having a front edge intended to be positioned at a front side of a person and a rear edge intended to be positioned at a rear side of a person. The absorbent article comprises a liquid pervious topsheet, a liquid impervious backsheet, and an absorbent material between the topsheet and the backsheet. At least a first spacer element is included between the topsheet and the backsheet. The spacer element has a top side facing the topsheet, a backside facing the backsheet, and a number of lateral sides between the topside and the backside. The absorbent material extends along at least two opposite lateral sides of the first spacer element. The first spacer element is configured to guide liquid to the absorbent material upon wetting of the absorbent article.

By providing at least a first spacer element, which is configured to guide liquid to the absorbent material upon wetting of the absorbent article, between the topsheet and the backsheet and with absorbent material extending along at least two opposite lateral sides of the first spacer element, upon wetting of the absorbent article a channel is created at the corresponding location of the first spacer element, such that liquid can be distributed and absorbed in an improved manner. A quantity of liquid can be temporarily held in the formed channel, and the chance of liquid overflow and leakage during a liquid insult is decreased. This is because the absorbent article absorbs no or less liquid at the corresponding location of the first spacer element, and as a result it expands less in volume at the corresponding location of the first spacer element compared to an absorbent material area extending along the at least two lateral sides, such that a valley is created at the location of the first spacer element. In this manner, the manufacturing process may be simplified, and the manufacturing cost may be reduced compared to an absorbent article with channels of the prior art, meanwhile an absorbent article with good liquid distribution and absorbent capacities can still be provided.

Preferably, the first spacer element is configured to absorb no or less liquid than a same volume of the absorbent material, upon wetting. Preferably, the first spacer element has at least an outer surface which is liquid-impervious. However, typically the first spacer element may be made entirely out of a non-liquid absorbing material. More generally, the first spacer element may be made of a material configured to absorb no or less liquid than the absorbent material. Preferably the material of the spacer element has a water absorption capacity which is at least 50% lower that the water absorption capacity of the absorbent material.

In an exemplary embodiment, the first spacer element is an elongated element, such that an elongated channel is formed upon wetting.

In an exemplary embodiment, the absorbent article has a crotch region in between the front edge and the rear edge, and the first spacer element extends from the crotch region in the direction of the front and/or rear edge. In this manner, liquid absorbent and distribution capacities is improved throughout the entire absorbent article in both front and rear portions.

In an exemplary embodiment the first spacer element extends in a longitudinal direction of the absorbent article. In this manner, liquid absorbent and distribution capacities in the longitudinal direct of the absorbent article are improved.

In an exemplary embodiment an angle between the first spacer element and the longitudinal direction of the absorbent article is smaller than 10°, preferably smaller than 5°. In this manner, liquid absorbent and distribution capacities in the longitudinal direct of the absorbent article are improved. Moreover, chances of liquid leaking out of the absorbent article at the longitudinal edges thereof are reduced.

In an exemplary embodiment, the first spacer element is attached to the topsheet and/or to the backsheet, which allows the formation of channel with a sufficient depth upon wetting of the absorbent article. In addition, the structure of the absorbent core is more stable and integrated/interconnected.

In an exemplary embodiment, the absorbent material is part of an absorbent core comprising a top core wrap sheet and a back core wrap sheet with the absorbent material positioned in between the top core wrap sheet and the bottom core wrap sheet. In such an embodiment, the first spacer element may be attached to the top core wrap sheet and/or to the back core wrap sheet, which may further improve the formation of a channel with a sufficient depth upon wetting of the absorbent core. In addition, the structure of the absorbent core is more stable and integrated/interconnected.

In exemplary embodiments, the spacer element may be made of waste material, for example waste from other layers of the absorbent article. Optionally the waste material may be treated mechanically (e.g. milled or cut) and/or chemically (e.g. coated). For example, the spacer element may be made of any one or any combination of the following materials: a non-water-absorbing polymer material such as a PE or PP material, chemically and/or mechanically treated fibers such as cellulose fibers.

In an exemplary embodiment, the absorbent article has a length between the front edge and the rear edge, and the first spacer element has a length which is at least 5%, preferably at least 10%, more preferably at least 20%, and even more preferably at least 30% of the length of the absorbent article.

In some cases, the length may even be larger than 50% of the length of the absorbent core. This improves the liquid distribution over a large area of the absorbent article.

In an exemplary embodiment, the absorbent article has a transverse crotch line dividing the absorbent core in a front portion and a rear portion on either side of the transverse crotch line, and the first spacer element extends in the front portion and in the rear portion, which allows a better liquid distribution between the front and rear portion of the absorbent article.

In an exemplary embodiment, the absorbent article further comprises a second spacer element between the topsheet and the backsheet. In this manner the liquid distribution and absorbent capacities are further improved.

In an exemplary embodiment, the second spacer element is an elongated element, such that an elongated channel is formed upon wetting.

In an exemplary embodiment the second spacer element extends in a longitudinal direction of the absorbent article. In this manner, liquid absorbent and distribution capacities in the longitudinal direct of the absorbent article are improved.

In an exemplary embodiment an angle between the second spacer element and the longitudinal direction of the absorbent article is smaller than 10°, preferably smaller than 5°. In this manner, liquid absorbent and distribution capacities in the longitudinal direct of the absorbent article are improved. Moreover, chances of liquid leaking out of the absorbent article at the longitudinal edges thereof are reduced.

In an exemplary embodiment, the absorbent article has a longitudinal center line dividing the absorbent article in a first longitudinal portion and a second longitudinal portion on either side of the longitudinal center line. The first spacer element is arranged in the first longitudinal portion and the second spacer element is arranged in the second longitudinal portion. Preferably the first and the second spacer element extend symmetrically with respect to the longitudinal center line. In this manner the liquid distribution and absorbent capacities are improved on both longitudinal portions of the absorbent article.

In an exemplary embodiment, also the second spacer element extends in the front portion and in the rear portion, which further improves the liquid distribution between the front and rear portion of the absorbent article.

In an exemplary embodiment, the absorbent article has a transverse crotch line dividing the absorbent core in a front portion and a rear portion on either side of the transverse crotch line, and the absorbent article further comprises a third spacer element between the topsheet and the backsheet. The first and second spacer elements extend at least in the front portion and the third spacer element extends at least in the rear portion. In this manner, the absorbent article may be tailored for male user, as during a liquid insult of a male user the volume of liquid is larger in the front portion than in the rear portion.

In an exemplary embodiment, the absorbent article further comprises a fourth spacer element between the topsheet and the backsheet. The fourth spacer element extends at least in the rear portion, and preferably the third and the fourth spacer element are arranged symmetrically with respect to a longitudinal center line of the absorbent article, which further improves the liquid distribution and absorbent capacities in the rear portion of the absorbent article.

In an exemplary embodiment, a maximum distance between the first and the second spacer element is different from a maximum distance between the third and the fourth spacer element. By having a different distance between the spacer elements in the front portion and in the rear portion, it is possible to tailor the absorbent article to the wearer. For example, for a male person the maximum distance may be larger in the front portion than in the rear portion, whilst for a female person the maximum distance may be larger in the rear portion than in the front portion. Further it is possible to optimize the difference between the front and the rear portion for obtaining an unisex absorbent article.

In an exemplary embodiment, the first and the second spacer element diverge in a direction of the front edge and/or the rear edge, which allows better liquid communication between the left/right portions of absorbent article near the front edge and/or the rear edge to the crotch region of the absorbent article.

In an exemplary embodiment, the first and second spacer elements together form a substantially X-shaped zone. In that manner, immediately after wetting, liquid is guided in the first and/or second elongate channel from left to right and/or from right to left, respectively, whilst flowing towards the crotch region or away from the crotch region, improving the liquid distribution, whereupon the liquid can be absorbed by the absorbent material. Further, by making the first and second attachment zones cross the longitudinal center line, the zones may be longer compared to similar zones extending parallel to the longitudinal center line, resulting in a larger liquid distribution zone.

In an exemplary embodiment, a maximum distance between the first and the second spacer element is between 5 and 70% of the width of the absorbent article, more preferably between 10 and 50%.

In an exemplary embodiment, the length of the first and second spacer is larger than 10% of the length of the absorbent article, more preferably larger than 20%, even more preferably larger than 30%, which allows formation of a channel sufficient long enough over a longitudinal dimension of the absorbent article and a better liquid distribution over the absorbent article.

In an exemplary embodiment, substantially no absorbent material is present between the first spacer element and the topsheet, and/or between the first spacer element and the backsheet, which allows the formation of channel with a sufficient depth upon wetting of the absorbent article.

In an exemplary embodiment, the first spacer element extends, seen in the transverse direction of the absorbent article, over a transverse distance which is at least 1 mm, preferably at least 3 mm, more preferably at least 4 mm, even more preferably at least 5 mm, most preferably at least 6 mm. In that manner the channels created upon wetting will be sufficiently wide to cause a good liquid distribution. Preferably, the first spacer element extends, seen in the transverse direction of the absorbent article, over a transverse distance which is smaller than 20 mm, more preferably smaller than 10 mm.

In an exemplary embodiment, the first spacer element extends, seen in the thickness direction of the absorbent article, over a distance which is at least 0.5 mm, preferably at least 1 mm, more preferably at least 2 mm, which allows the formation of channel with a sufficient depth upon wetting of the absorbent article.

In an exemplary embodiment, the absorbent material comprises cellulosic fluff pulp and/or superabsorbent particles.

The spacer element may be provided with an indication, e.g. a color and/or a pattern which is different from the color and/or pattern of topsheet and/or backsheet, and which is visible through the topsheet and/or backsheet, allowing a user to visually distinguish the channel. Alternatively this indication may be arranged on the topsheet 100, on the backsheet 200, or on any sheet in between the topsheet 100 and the backsheet 200, as long as it is visible for a user. As the sheets may be partially transparent, the print may be arranged on the spacer element or on a sheet in between the topsheet and the backsheet, as long as it is visible through the topsheet and/or the backsheet. Preferably the print is visible when looking at the topsheet of the absorbent article.

According to a second aspect of the invention, there is provided an absorbent core comprising a top core wrap sheet, a back core wrap sheet, and absorbent material positioned in between the top core wrap sheet and the bottom core wrap sheet. At least a first spacer element is included between the top core wrap sheet and the back core wrap sheet, the first spacer element being configured to guide liquid upon wetting of the absorbent core. The spacer element has a topside facing the topsheet, a backside facing the backsheet, and a number of lateral sides between the topside and the backside. The absorbent material extends along at least two opposite lateral sides of the first spacer element.

By providing at least a first spacer element which guides liquid upon wetting of the absorbent core, between the top core wrap sheet and the back core wrap sheet and with absorbent material extending along at least two opposite lateral sides of the first spacer element, upon wetting of the absorbent core a channel is created at the corresponding location of the first spacer element, such that liquid can be distributed and absorbed in an improved manner. A quantity of liquid can be temporarily held in the formed channel, and the chance of liquid overflow and leakage during a liquid insult is decreased. This is because the absorbent core absorbs no or less liquid at the corresponding location of the first spacer element, and as a result it expands less in volume at the corresponding location of the first spacer element. In this manner, the manufacturing process may be simplified and the manufacturing cost may be reduced compared to absorbent cores with channels of the prior art. Meanwhile an absorbent core with good liquid distribution and absorbent capacities can still be provided.

The features described above for the absorbent article may, where possible, also be included in the absorbent core. For example, the absorbent core may be provided with a plurality of spacer elements as described above.

BRIEF DESCRIPTION OF FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which.

DESCRIPTION OF EMBODIMENTS

Figure 1A:
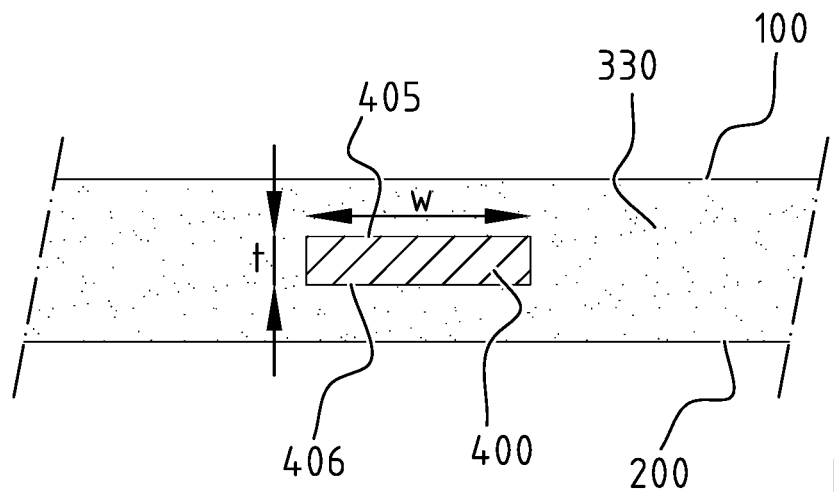
FIG. 1A is a schematic cross-section of an exemplary embodiment of an absorbent article.

As used herein, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to permanently absorb and/or retain bodily exudates.

"Absorbent component" as used herein refers to a structural constituent of an absorbent article, e.g., a piece of an absorbent core, such as one of multiple pieces in a multi-piece absorbent core.

"Absorbent element" as used herein refers to a part of a functional constituent of an absorbent structure, e.g., a acquisition layer, a dispersion layer, core layer or a release structure formed of a material or materials having particular liquid handling characteristics suitable for the specific function.

"Absorbent fibrous polymer material" as used herein refers to an absorbent polymer material which is in thread-like from such as fibers, filaments, and the like so as to be less flowable in the dry state than particulates.

"Absorbent insert" as used herein refers to a device adapted for insertion into an "Absorbent layer" as used herein refers to a term referring to a discrete, identifiable sheet-like or web-like element of an absorbent article which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g. bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Absorption rate" as used herein refers to the rate of absorption of liquid, i.e. the amount of liquid which is absorbed per unit of time, typically by an absorbent component, element and/or absorbent layer of the absorbent article, structure and/or core.

"Acquisition layer", "acquisition region", "acquisition surface" or "acquisition material" and the like as used herein refer to the layer overlying the absorbent core having a faster liquid uptake and/or distribution capability.

"Absorbency" is the ability of a material to take up fluids by various means including capillary, osmotic, solvent, chemical and/or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure and/or vacuum; a web of fibers produced by airlaying is herein referred to an "airlaid"; an airlaid web bonded by one or more techniques to provide fabric integrity is herein referred to an "airlaid nonwoven".

"Apparent density", "density" as used herein refers to the basis weight of the sample divided by the caliper with appropriate unit conversions incorporated therein. Apparent density used herein has the unit $g/cm^3$.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, g/m² or gsm.

"Bodily exudates", "body exudates", "bodily fluids", "body fluids", "bodily discharges", "body discharges", "fluid(s)", "liquid(s)", "fluid(s) and liquid(s) and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc), altering the chemical structure of the fibers themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garment s, baby diapers and pants and adult incontinence garments.

"Crotch region" of an absorbent article as used herein refers to about 50% of the absorbent article's total length (i.e., in the y-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them in soluble.

"Diaper", "conventional diaper", "diaper-like", "diaper-like garment" and the like as used herein are used interchangeably and refer to disposable absorbent articles, which typically include a front waist portion and a back waist portion which may be releasable connected about the hips of the wearer during use by conventional fasteners such as adhesive tape fasteners or hook and loop type fasteners. In use, the article is positioned between the legs of the wearer and the fasteners are releasable attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Dispersion layer", "dispersion region", "dispersion surface" or "dispersion material" and the like as used herein refer to the layer overlying the absorbent core having a faster liquid uptake and dispersion capability.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Drylaying" as used herein refers to a process for making a nonwoven web from dry fiber; these terms apply to the formation of carded webs, as well as to the air laying formation of random webs; a web of fibers produced by drylaying is herein referred to as a "drylaid"; a drylaid web bonded by one or more techniques to provide fabric integrity is herein referred to a "drylaid nonwoven".

"Dry strength" as used herein refers to the strength of ajoint determined in dry state conditions, immediately after drying under specified conditions or after a period of conditioning in the standard laboratory atmosphere.

"Essentially cellulose free" or "little to no cellulose fibers" as used herein refers to an absorbent article, structure, core component and/or element containing less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Essentially fluffless" or "little to no fluff pulp" as used herein refers to an absorbent article, structure, core, component and/or element containing less than 20% by weight fluff pulp, less than 10% fluff pulp, less than 5% fluff pulp, no fluff pulp, or no more than an immaterial amount of fluff pulp which do not materially affect the thinness, flexibility or absorbency thereof.

"Fabric" as used herein refers to a sheet structure made from fibers, filaments and/or yarns.

"Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width; "Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" or "Pulp fluff" as used herein refers to wood pulp specially prepared to be drylaid. The fibers can be either natural or synthetic or a combination thereof.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"High loft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to gather, bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and/or faces the wearer facing layer; conversely, the term "lower" refers to the layer of the absorbent article which is nearest to and/or faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the f low of a liquid from one absorbent element or component to another absorbent element or component by channel flow action.

"Mechanical bonding" as used herein refers to a method of bonding fibers by entangling them. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or nonrefastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Release structure", "release region", "release surface" or "release material" and the like as used herein are used interchangeably and refer to a structure in fluid communication with the absorbent core having a larger relative liquid absorption capacity and/or rate allowing it to quickly take up, temporarily hold and releasing liquids.

"Resin" as used herein refers to a solid or semisolid polymeric material.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibers produced by weaving is herein referred to as a "woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (they-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or nonwoven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The same or similar features and components are indicated with the same reference numerals throughout the figures.

Figure 1B:
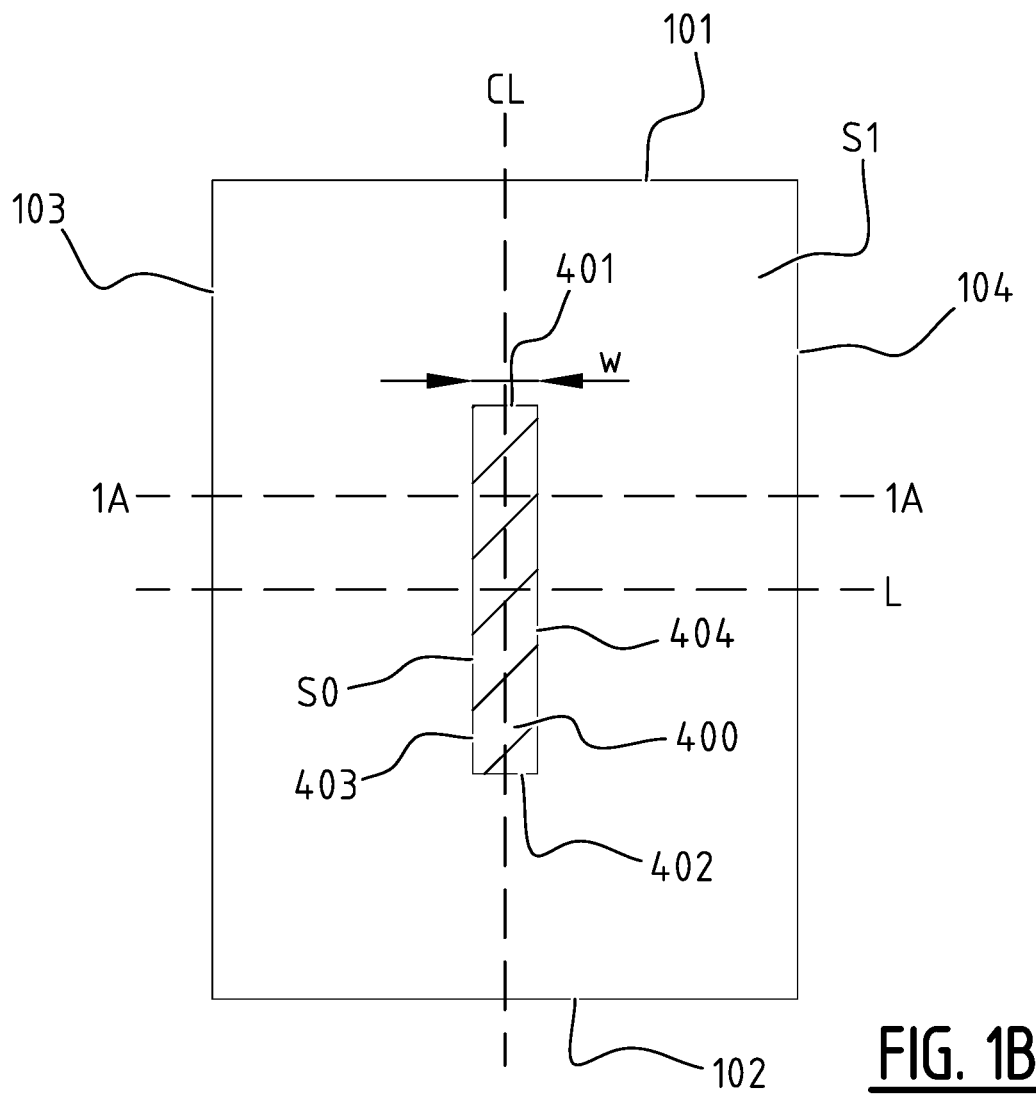
FIG. 1B is a top plan view of the absorbent article of FIG. 1A.

FIGS. 1A and 1B illustrate an exemplary embodiment of an absorbent article, here a diaper. FIG. 1A shows a cross-section of the absorbent article along line 1A-1A of FIG. 1B, and FIG. 1B shows the absorbent article in its flat out, un-contracted state with the wearer side facing the viewer. The skilled person understands that the absorbent article may also be a pant or an adult incontinence garment or the like. The absorbent article has a front edge 101 intended to be positioned at a front side of a person and a rear edge 102 intended to be positioned at a rear side of a person. The absorbent article also has a first longitudinal edge 103 and a second longitudinal edge 104. The absorbent article comprises a liquid pervious topsheet 100, a liquid impervious backsheet 200, and an absorbent material 330 between the topsheet 100 and the backsheet 200. The absorbent material 330 comprises cellulosic fluff pulp and/or superabsorbent particles.

A spacer element 400 of an elongated shape is included between the topsheet 100 and the backsheet 200. The spacer element 400 is made of a material configured to absorb no or less liquid than the absorbent material 330 upon wetting of the absorbent article. In practice the liquid is typically urine. However, for determining whether a material is suitable for the spacer element 400, the absorption properties for water may be considered. Preferably the material does not absorb water or absorbs at least 80 percent less water compared to a same volume of absorbent material used in the absorbent article. In exemplary embodiments, the spacer element may be made of waste material, for example waste from other layers of the absorbent article. Optionally the waste material may be treated mechanically (e.g. milled or cut) and/or chemically (e.g. coated). For example, the spacer element 400 may be made of any one or any combination of the following materials: a non-water-absorbing polymer material such as a PE or PP material, chemically and/or mechanically treated fibers such as cellulose fibers. For example, the spacer element may be a possibly breathable polyethylene (PE) or polypropylene (PP) layer, e.g. a coated polyethylene or polypropylene film.

The spacer element 400 has a topside 405 facing the topsheet 100, a backside 406 facing the backsheet 200, and a plurality of lateral sides between the topside 405 and the backside 406. Here the lateral sides consist of a front side 401, a rear side 402, and two longitudinal sides 403, 404. The absorbent material 330 extends along at least two opposite lateral sides of the spacer element 400. In the embodiment of FIGS. 1A and 1B the absorbent material 330 extends along all four lateral sides 401, 402, 403, 404, and there even some absorbent material above the topside 405 and below the bottom side 406. In other words, from a 3-D perspective, the spacer element 400 may be surrounded by the absorbent material 330. Seen from a top view, a contour of the spacer element is adjacent to the absorbent material 330. However, in preferred embodiments substantially no absorbent material 330 is present between the topside 405 and the topsheet 100 and between the backside 406 and the backsheet 200. Upon wetting of the absorbent article, the absorbent material 330 absorbing liquid expands in volume. As the spacer element 400 absorbs no or less liquid, the absorbent article expands less in volume at the corresponding location of the spacer element 400. As a result, a channel is created at the corresponding location of the spacer element 400 of the absorbent article. The created channel facilitates liquid distribution towards the absorbent material 330 and an improved absorption by the absorbent material 330. Therefore, the chance of liquid overflow and leakage during a liquid insult is decreased. Since the absorbent article has a simple structure, the manufacturing process may be simplified and the manufacturing cost may be reduced, compared to other absorbent article with channels of the prior art, while an absorbent article with good liquid distribution and absorbent capacities can still be provided. In that regard it is noted that in the embodiment of FIGS. 1A and 1B no core wrap is used to encapsulate the absorbent material 330, and that the absorbent material is directly included between the topsheet 100 and the backsheet 200.

The absorbent article has a crotch region in between the front edge 101 and the rear edge 102, and a transverse crotch line L dividing the absorbent article into a front portion and a rear portion on either side of the transverse crotch line L. The absorbent article has a length between the front edge 101 and the rear edge 102. The spacer element 400 extends from the crotch region in the direction of the front edge 101 and the rear edge 102 in both the front portion and the rear portion, and has a length which is at least 20%, more preferably at least 30% of the length of the absorbent article. This embodiment allows a better liquid communication between the front portion and the rear portion of the absorbent article, and overall improved liquid absorption and distribution capacities of the absorbent article.

In other possible embodiments, the spacer element 400 may extend in the direction from the first longitudinal edge 103 to the second longitudinal edge 104 of the absorbent article, which allows a better liquid distribution between left and right portions of absorbent article. It is also possible for the spacer element to extend under a small angle with respect to the longitudinal direction of absorbent article, e.g. an angle between 5 and 10°.

Seen in the transverse direction of the absorbent article, the spacer element 400 extends over a transverse distance w which is at least 1 mm, preferably at least 3 mm, more preferably at least 4 mm, even more preferably at least 5 mm, most preferably at least 6 mm. In this manner the channel created upon wetting will be sufficiently wide to cause a good liquid distribution. Preferably, the width is smaller than 20 mm, more preferably smaller than 15 mm. The width w of the spacer element 400 may be constant through substantially the whole length of the spacer element 400 or may vary along its length. Preferably the spacer element 400 is arranged symmetrically with respect to the longitudinal center line CL of absorbent article. Here the spacer element 400 is arranged on the longitudinal center line CL.

The spacer element 400 extends, seen in the thickness direction of the absorbent article, over a distance which is at least 0.5 mm, preferably at least 1 mm, more preferably at least 2 mm. The thickness t of the spacer element 400 may be constant through substantially the whole length of the spacer element 400 or may vary along its length.

In the embodiment of FIGS. 1A and 1B, seen in a cross-section view, the spacer element 400 is not attached to the topsheet 100 and/or to the backsheet 200, and there is absorbent material 330 between the spacer element 400 and the topsheet 100 and between the spacer element 400 and the backsheet 200. However, the spacer element 400 may be attached to the absorbent material above and below, e.g. by glue, which improves the overall structural stability of the absorbent article. In another possible embodiment (see FIGS. 3A-3C discussed below), the spacer element 400 is attached to the topsheet 100 and/or to the backsheet 200. That's to say, there may be no absorbent material 330 between the spacer element 400 and the topsheet 100, and/or between the spacer element 400 and the backsheet 200. The attachment may be realized by adding binder layers, such as glue, to strengthen the bond between the spacer element 400 and the topsheet 100 and/or backsheet 200. Also other bonding techniques may be used, such as ultrasonic bonding, heat bonding, pressure bonding, and combinations thereof. In this manner, upon wetting of the absorbent article, the difference in thickness of the absorbent article is even larger, between an area corresponding to the spacer element S0 and an area without the spacer element 51. As a result, the formed channel has a sufficient depth, is able to hold more liquid and allows better liquid distribution and absorbance. In addition, the structure of the absorbent article is more stable and more integrated/interconnected, which improves the stability of the absorbent article and wearing comfort.

Seen from a top view, the spacer element 400 has a center line, which is a straight line. In other possible embodiments, the center line of the spacer element 400 may have other shapes, e.g. a curve, or a polyline. The center line is a line which is at the same distance of opposite sides 403, 404 of the spacer element 400 and which preferably extends in a length direction of the spacer element 400.

The channel created by the spacer element 400 may be indicated with a color and/or with a pattern which is different from the color and/or pattern of topsheet 100. More in particular the area of the channel may comprise a print allowing a user to visually distinguish the channel. This print may be arranged on the spacer element 400, on the topsheet 100, on the backsheet 200, or on any sheet in between the topsheet 100 and the backsheet 200, as long as it is visible for a user. As the sheets may be partially transparent, the print may be arranged on the spacer element 400 or on a sheet in between the topsheet 100 and the backsheet 200, as long as it is visible through the topsheet 100 and/or the backsheet 200. Preferably the print is visible when looking at the topsheet 100 of the diaper.

Figure 2A:
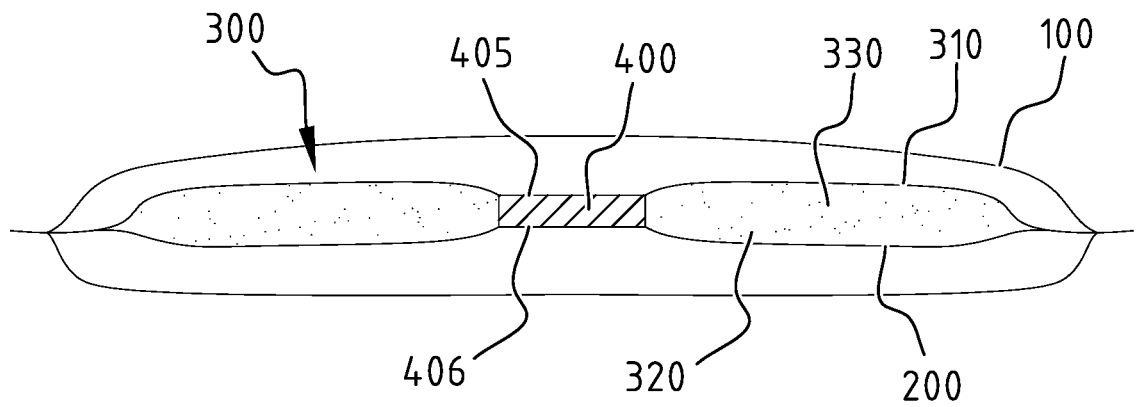
FIG. 2A is a schematic cross-section of another exemplary embodiment of an absorbent article.
Figure 2B:
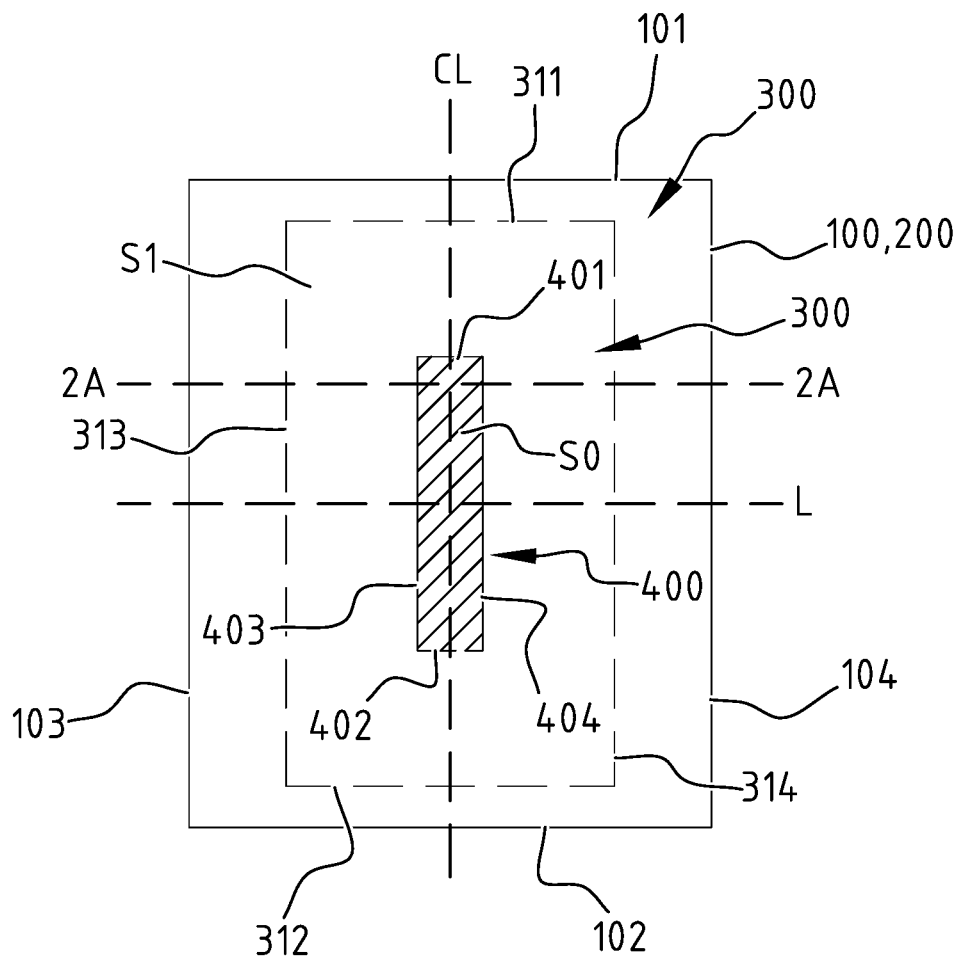
FIG. 2B is top plan view of the absorbent article of FIG. 2A.

FIGS. 2A and 2B illustrate another exemplary embodiment of an absorbent article, here a diaper. FIG. 2A shows the cross-section of the absorbent article along line 2A-2A of FIG. 2B, and FIG. 2B shows a top view of the absorbent article in its flat out, un-contracted state with the wearer side facing the viewer. In this embodiment, the absorbent material 330 is part of an absorbent core 300 comprising a top core wrap sheet 310 and a back core wrap sheet 320 with the absorbent material 330 positioned in between the top core wrap sheet 310 and the bottom core wrap sheet 320.

The absorbent article comprises a liquid pervious topsheet 100, a liquid impervious backsheet 200, and the absorbent core 300 between the topsheet 100 and the backsheet 200. The absorbent core 300 has a rectangular shape, having a front edge 311, a rear edge, 312, a first longitudinal edge 313, and a second longitudinal edge 314. A spacer element 400 is included between the top core wrap sheet 310 and the back core wrap sheet 320. The spacer element 400 is made of a material configured to absorb no or less liquid than the absorbent material 330 upon wetting of the absorbent core 300. The spacer element 400 has a topside 405 facing the top core wrap sheet 310 and the topsheet 100, a backside 406 facing the back core wrap sheet 320 and the backsheet 200, and a plurality of lateral sides between the topside 405 and the backside 406. Here the lateral sides consist of a front side 401, a rear side 402, and two longitudinal sides 403, 404. The absorbent material 330 extends along at least two lateral opposite sides 401, 402, 403, 404 of the spacer element 400. Seen from a top view, a contour of the spacer element 400 is adjacent to the absorbent material 330.

The spacer element 400 is attached to the top core wrap sheet 310 and to the back core wrap sheet 320. There may be substantially no absorbent material 330 between the spacer element 400 and the top core wrap sheet 310, and/or between the spacer element 400 and the back core wrap sheet 320. The attachment may be realized by adding binder layers, such as glue, to strengthen the bond between the spacer element 400 and the top core wrap sheet 310 and/or back core wrap sheet 320. Also other bonding techniques may be used, such as ultrasonic bonding, heat bonding, pressure bonding, and combinations thereof. In this manner, upon wetting of the absorbent core 300, the difference in thickness of the absorbent core is even larger, between the area corresponding to the spacer element S0 and the area without the spacer element Sl. As a result, the formed channel has a sufficient depth, is able to hold more liquid and allows better liquid distribution and absorbance. In addition, the absorbent article is even more structured and interconnected, resulting in a more stable channel forming and even less leakage risks. In another possible embodiment, the spacer element 400 is not attached to the top core wrap sheet 310 and/or to the back wrap sheet 320, and there may be absorbent material 330 between the spacer element 400 and the top core wrap sheet 310 and between the spacer element 400 and the back core wrap sheet 320. However, the spacer element 400 may be attached to the absorbent material 330 above and/or below, e.g. by glue or any other suitable bonding technique, which improves the overall structural stability of the absorbent core.

The absorbent core 300 has a crotch region in between the front edge 311 and the rear edge 312, and a transverse crotch line L dividing the absorbent core 300 into a front portion and a rear portion on either side of the transverse crotch line L. The absorbent core 300 has a length between the front edge 311 and the rear edge 312. The spacer element 400 extends from the crotch region in the direction of the front edge 311 and the rear edge 312 of the absorbent core in both the front portion and the rear portion, and has a length which is at least 20% more preferably at least 30% of the length of the absorbent core 300.

Upon wetting of the absorbent article, the absorbent material absorbing liquid expands in volume. As the spacer element 400 absorbs no or less liquid, the absorbent core 300 expands less in volume at the corresponding location of the spacer element S0. As a result, a channel is created at the corresponding location S0 of the spacer element 400 of the absorbent core. The created channel facilitates liquid distribution over the absorbent core 300, and a larger quantity of liquid can be temporarily held in the created channel. Since the absorbent core has a simple structure, the manufacturing process may be simplified and the manufacturing cost may be reduced, compared to other absorbent core with channels of the prior art, while an absorbent core with good liquid distribution and absorption capacities can still be provided. In addition, the absorbent core 300 can be directly used in the manufacturing of absorbent articles of various types.

The absorbent article may further comprise an acquisition and distribution layer ADL (not shown) positioned between the absorbent core 300 and the liquid pervious topsheet 100. This serves to slow down the flow so that the liquid has adequate time to be absorbed by and evenly distributed over the absorbent core 300. The absorbent article may further comprise adhesive between the absorbent core 300 and the ADL, and/or the absorbent article comprises adhesive between the ADL and the liquid pervious topsheet 100. If no ADL is present the absorbent article may comprise adhesive between the absorbent core 300 and the topsheet 100.

Figure 3A:
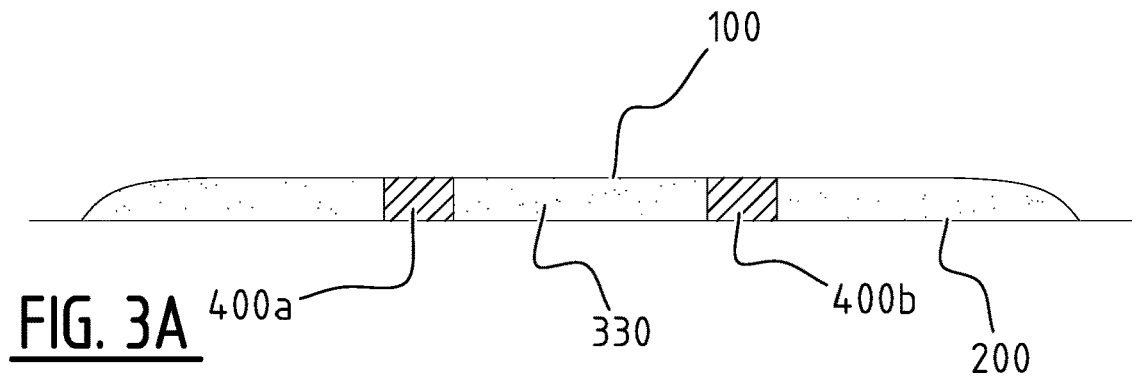
FIGS. 3A and 3B are schematic cross-sections of another exemplary embodiment of an absorbent article in an unwetted and wetted state, respectively.
Figure 3B:
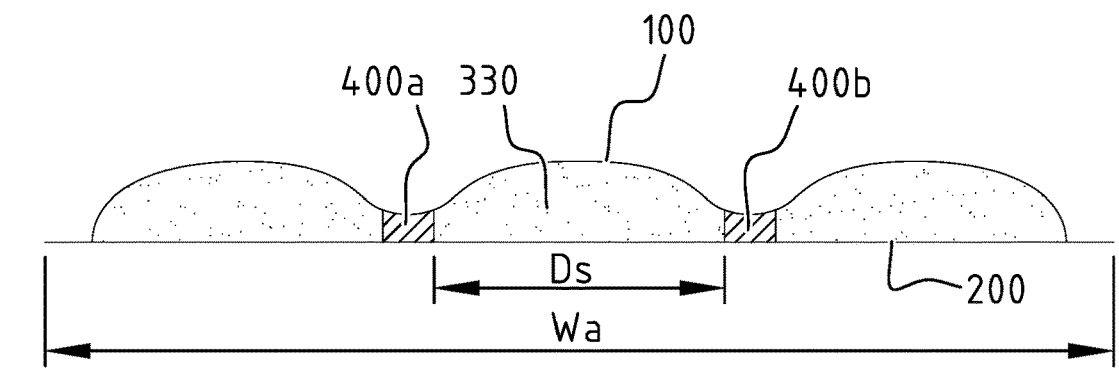
Figure 3C:
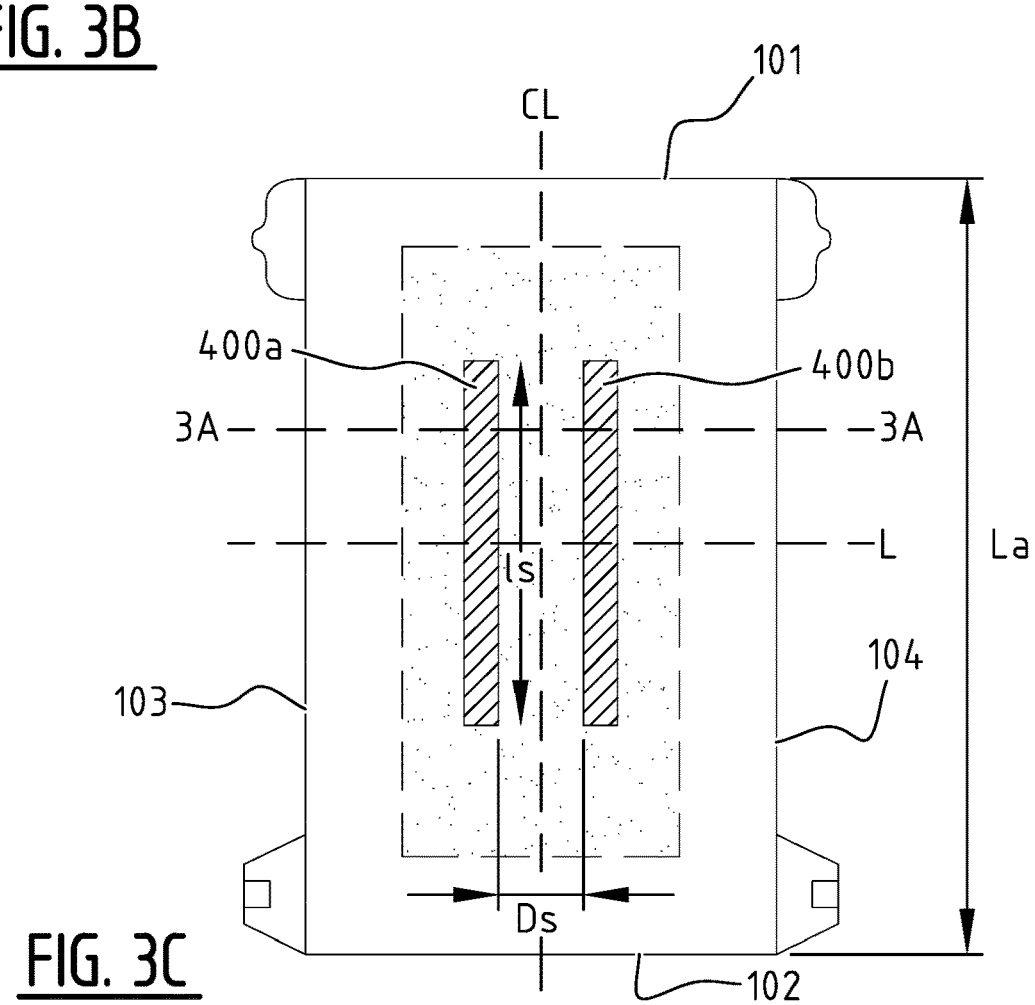
FIG. 3C is top plan view of the absorbent article of FIG. 3A.

FIGS. 3A, 3B and 3C illustrate another exemplary embodiment of an absorbent article. FIGS. 3A and 3B show a cross-section of the absorbent article along line 3A-3A of FIG. 3C, in a dry and wetted state, respectively, and FIG. 3C shows a top view of the absorbent article in its flat out, un-contracted state with the wearer side facing the viewer. The absorbent article comprises a liquid pervious topsheet 100, a liquid impervious backsheet 200, and the absorbent material 330 between the topsheet 100 and the backsheet 200. Two spacer elements 400a, 400b are arranged at a distance of each other between the topsheet 100 and the backsheet 200. The first and second spacer element 400a, 400b are configured to guide liquid to the absorbent material 330 upon wetting of the absorbent article. This may be realized by configuring the first and second spacer element 400a, 400b to absorb no or less liquid than a same volume of the absorbent material 330. The first and second spacer element may have at least an outer surface which is liquid-impervious. More preferably the entire first and second spacer elements are liquid impervious. The first spacer element may be made of a material configured to absorb no or less liquid than the absorbent material.

The absorbent article has a longitudinal center line CL dividing the absorbent article in a first longitudinal portion and a second longitudinal portion on either side of the longitudinal center line, and the first spacer element is arranged in the first longitudinal portion and the second spacer element is arranged in the second longitudinal portion, preferably symmetrically with respect to the longitudinal center line CL. Preferably, the first and second spacer element 400a, 400b extend in the front portion and in the rear portion. In the illustrated embodiment the first and second spacer element are substantially parallel. However, in other possible embodiments the first and the second spacer element diverge in a direction of the front edge and/or the rear edge. Preferably, a maximum distance Ds between the first and the second spacer element is between 15 and 70% of the width Wa of the absorbent article, more preferably between 20 and 50%. Preferably, the length is of the first and second spacer is larger than 10% of the length La of the absorbent article, more preferably larger than 20%, even more preferably larger than 30%.

Figure 4:
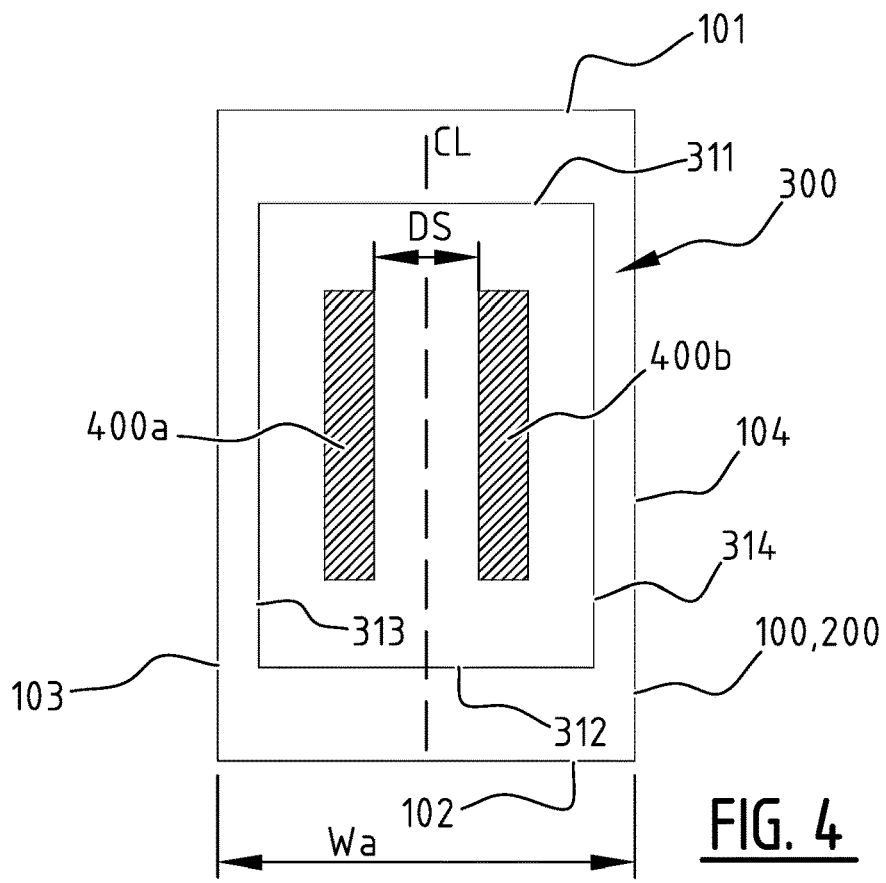
FIGS. 4-10 illustrate other exemplary embodiments of an absorbent article comprising one or more spacer elements.

FIG. 4 illustrates another exemplary embodiment of an absorbent article comprising a first and second spacer element 400a, 400b between the topsheet 100 and the backsheet 200. The absorbent article comprises a liquid pervious topsheet 100, a liquid impervious backsheet 200, and an absorbent core 300 between the topsheet 100 and the backsheet 200. The absorbent core 300 may be similar to the absorbent core 300 of FIGS. 2A and 2B with this difference that a second spacer element 400b is provided. The absorbent core 300 has rectangular shape, having a front edge 311, a rear edge, 312, a first longitudinal edge 313, and a second longitudinal edge 314. The first spacer element 400a and the second spacer element 400b are included between the top core wrap sheet 310 and the back core wrap sheet 320. The absorbent material 330 extends along the lateral sides of the first spacer element 400a and the second spacer element 400b, in a similar manner as described above for FIGS. 2A and 2B. Seen from a top view, contours of the first spacer element 400a and the second spacer element 400b are adjacent to the absorbent material 330.

The absorbent article has a longitudinal center line CL dividing the absorbent article in a first longitudinal portion and a second longitudinal portion on either side of the longitudinal center line CL. The first spacer element 400a is arranged in the first longitudinal portion and the second spacer element 400b is arranged in the second longitudinal portion. The first and the second spacer element 400a, 400b extend symmetrically with respect to the longitudinal center line CL. In this manner the liquid distribution and absorbent capacities of the absorbent core are improved on both longitudinal portions of the absorbent core. The first and the second spacer element 400a, 400b extend in parallel in the longitudinal direction of the absorbent core 300, from the crotch region of the absorbent core to the front and the rear transverse edge 311, 312 of the absorbent core, in both the front portion and the rear portion of the absorbent core. The first spacer element 400a and the second spacer element 400b have substantially the same length, which is at least 10%, preferably at least 20%, more preferably at least 30% of the length of the absorbent core 300. Upon wetting of the absorbent core, two channels are created on both longitudinal portions of the absorbent core respectively.

Preferably, the first and second spacer element 400a, 400b extend in the front portion and in the rear portion. Preferably, a maximum distance Ds between the first and the second spacer element is between 5 and 70% of the width Wa of the absorbent article, more preferably between 10 and 50%. In the illustrated embodiment the first and second spacer element are substantially parallel. In another possible embodiment, the first and the second spacer element may diverge in a direction of the front edge 311 and/or the rear edge 312, which allows better liquid communication between the left/right portions of absorbent core near the front edge and/or the rear edge to the crotch region of the absorbent core.

Figure 5:
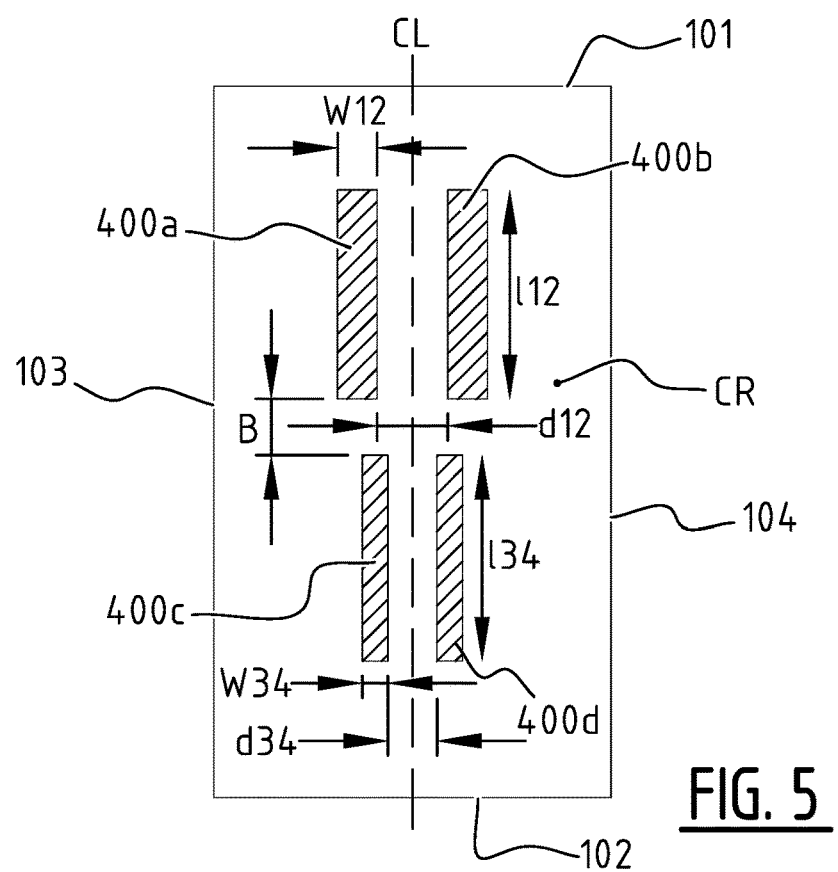

FIG. 5 illustrates another exemplary embodiment of an absorbent article further comprising a third spacer element 400c and a fourth spacer element 400d between the topsheet 100 and the backsheet 200. Like the first spacer element 400a and the second spacer element 400b, the third spacer element 400a and the fourth spacer element 400d may be included between the top core wrap sheet 310 and the back core wrap sheet 320 of the absorbent core 300 (cf. FIG. 4), or directly between the topsheet 100 and the backsheet 200 (cf. FIGS. 3A-3C). The spacer elements 400a, 400b, 400c, 400b may have similar properties as described above for embodiments with one or two spacer elements. All spacer elements 400a, 400b, 400c, 400d may be attached to the top core wrap sheet 310 or to the topsheet 100 (if no core wrap is present) and/or to the back core wrap sheet 320 or to the backsheet 200 (in no core wrap is present), and there may be substantially no absorbent material above and/or below each spacer element 400a, 400b, 400c, 400d. Upon wetting of the absorbent material, four channels are created.

The first and second spacer 400a, 400b elements extend next to each other from the crotch region CR in the direction of the front edge 101 in the front portion of the absorbent article. The third and fourth spacer elements 400c, 400d extend next to each other from the crotch region CR in the direction of the rear edge 101 in the rear portion of the absorbent article.

The first and the second spacer elements 400a, 400b are located a distance d12 of each other. Preferably the distance d12 is between 5 and 70% of the width of the absorbent article, more preferably between 10 and 50%. The first and second spacer elements 400a, 400b have substantially the same length 112, which is at least 5%, preferably at least 10% of the absorbent article. The first and second spacer elements 400a, 400b have substantially the same width w12, which is at least 2 mm, preferably at least 4 mm, more preferably at least 5 mm, even more preferably at least 6 mm, most preferably at least 7 mm. The first and the second spacer elements 400a, 400b are substantially parallel and run in the longitudinal direction of absorbent article. However, it is also possible for the first and the second spacer elements 400a, 400b to extend under a small angle with respect to the longitudinal direction of absorbent article, e.g. an angle between 5 and 10°. For example, the first and the second spacer elements 400a, 400b may be diverging slightly outwardly in the direction of front edge 101. The first and the second spacer elements 400a, 400b are arranged symmetrically with respect to a longitudinal center line CL of absorbent article.

The third and the fourth spacer elements 400c, 400d are located a distance d34 of each other, preferably the distance d34 is between 5 and 70% of the width of the absorbent article, more preferably between 10 and 50%. The third and the fourth spacer elements 400c, 400d have substantially the same length 134, which is at least 5%, preferably at least 10% of the absorbent article. The third and the fourth spacer elements 400c, 400d have substantially the same width w34, which is at least 1 mm, preferably at least 3 mm, more preferably at least 4 mm, even more preferably at least 5 mm, most preferably at least 6 mm. The third and the fourth spacer elements 400c, 400d are substantially parallel and run in the longitudinal direction of absorbent article. However, it is also possible for the third and the fourth spacer elements 400c, 400d to extend under a small angle with respect to the longitudinal direction of absorbent article, e.g. an angle between 5 and 10°. For example, the third and the fourth spacer elements 400c, 400d may be diverging slightly outwardly in the direction of rear edge 102. The third and the fourth spacer elements 400c, 400d are arranged symmetrically with respect to a longitudinal center line CL of the absorbent article.

Preferably d12 is different from d34, more preferably d12 is larger than d34, even more preferably d12 is at least 10% larger than d34. Optionally w12 may be different from w34, preferably w12 is larger than w34, even more preferably w12 is at least 1 mm or at least 10% larger than w34. Preferably 112 is different from 134, more preferably 112 is smaller than 134, even more preferably 112 is at least 10% smaller than 134. In this manner, the absorbent article is tailored for male user, as during a liquid insult of a male user the volume of liquid is larger in the front portion than in the rear portion. Further it is possible to optimize the differences between the front and the rear portion for obtaining a unisex absorbent article.

Preferably, the first spacer element 400a is separated from the third spacer element 400c by a distance B, and the second spacer element 400b is also separated from the fourth spacer element 400d by substantial the same distance. The distance is measure between the ends of spacer elements by a projection on the longitudinal center line. Preferably, the distance B is smaller than 40 mm, more preferably smaller than 25 mm, even more preferably smaller than 20 mm. In another embodiment, endpoints of the spacer elements 400a, 400b, 400c, 400d in the crotch region may be located on substantially the same transverse line L functioning as a fold line along which the diaper can be folded in two.

Figure 6:
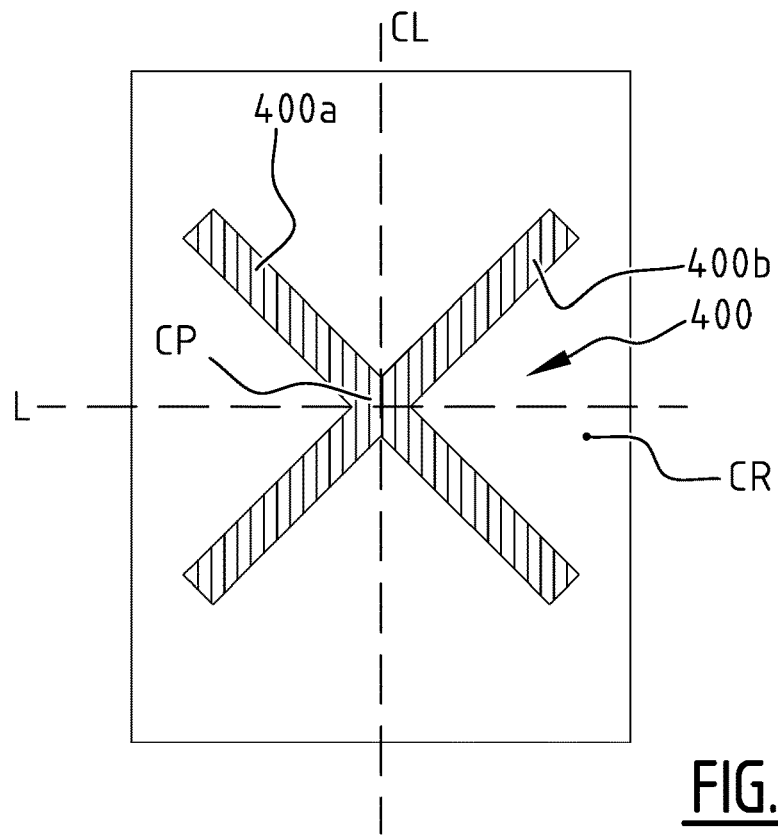

FIG. 6 illustrates an exemplary embodiment, in which the first and second spacer elements 400a, 400b together form a substantially X-shaped spacer element 400. The absorbent article comprises a liquid pervious topsheet 100, a liquid impervious backsheet 200, and an absorbent material 330 between the topsheet 100 and the backsheet 200. A first spacer element 400a and a second spacer element 400b of an elongated shape are included between the topsheet 100 and the backsheet 200. The first and second spacer elements 400a, 400b may also be provided as a single integral element 400. The spacer elements 400a, 400b may have similar properties as described above for other embodiments with one or two spacer elements. As in FIGS. 3A-3C, the first spacer element 400a and a second spacer element 400b may be attached to the topsheet 100 and/or backsheet 200, and there may be no absorbent material between the spacer elements and the topsheet, and/or between the spacer elements and the backsheet. Alternatively a core wrap may be provided as in the embodiment of FIG. 4. The first spacer element 400a extends from the front portion of the first longitudinal portion of the absorbent article to the rear portion of the second longitudinal portion of the absorbent article. The second spacer element 400b extends from the front portion of the second longitudinal portion of the absorbent article to the rear portion of the first longitudinal portion of the absorbent article. Seen from a top view, the first spacer element 400a and the second spacer element 400b form a crossing point CR Preferably, the crossing point CP is located on the longitudinal center line CL of the absorbent article, and/or the crossing point CP is located in the crotch region CR of the absorbent article. Together, the first and second spacer elements 400a, 400b form a substantially X-shaped zone. The overlapping region of the first and second spacer elements 400a, 400b are shared by the first and second spacer elements 400a, 400b. That's to say, physically the first and second spacer elements 400a, 400b share the same portion at the crossing point CR The contour of the X-shaped spacer element 400 is adjacent to the absorbent material 330. Upon wetting of the absorbent article, an X-shaped channel is formed.

Figure 7:
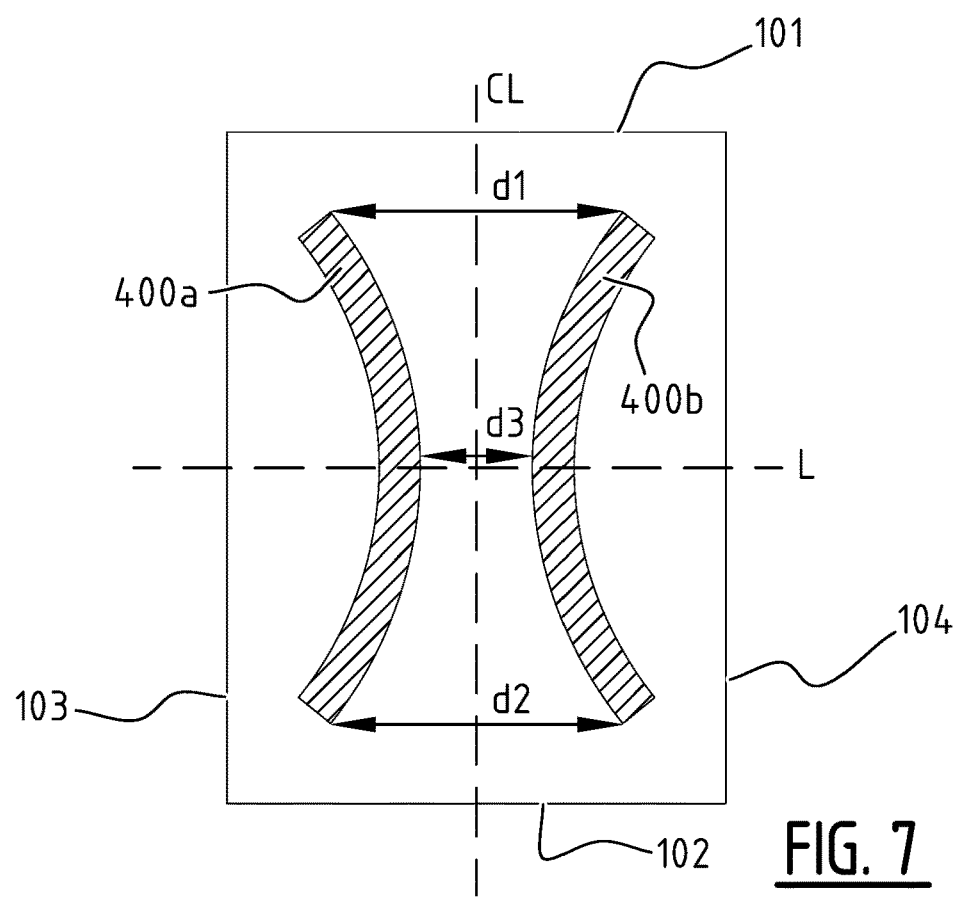

FIG. 7 illustrates an absorbent article comprising a first spacer element 400a and a second spacer element 400b of an elongated shape included between the topsheet 100 and the backsheet 200, as in FIGS. 3A-3C. Alternatively a core wrap may be provided as in the embodiment of FIG. 4. The spacer elements 400a, 400b may have similar properties as described above for other embodiments with one or two spacer elements. The first and the second spacer element 400a, 400b diverge in a direction of the front edge 101 and the rear edge 102, which allows better liquid communication between the left/right portions of absorbent article near the front edge and the rear edge to the crotch region of the absorbent article. The first spacer element and the second spacer element 400a, 400b have a curved-shape, and preferably are arranged symmetrically with respect to the longitudinal center line CL of the absorbent article. For example in FIG. 7, the first spacer element and the second spacer element 400a, 400b are concave towards the longitudinal center line CL of the absorbent article such that they bend towards the longitudinal center line CL. In other possible embodiments, the first spacer element and the second spacer element 400a, 400b may also be convex, such they bend away from the longitudinal center line CL, or they have any other suitable arrangement. In this embodiment, the maximum distance between the first spacer element and the second spacer element in the front portion d1 is substantially the same as the maximum distance between the first spacer element and the second spacer element in the rear portion d2. However it is also possible that maximum distance at the front portion d1 is different from the maximum distance at the rear portion d2, e.g. the maximum distance at the front portion d1 is 10% larger than the maximum distance at the rear portion d2. The minimum distance between the first spacer element and the second spacer element 400a, 400b d3 is preferably at least 5 mm. However in possible embodiments, the minimum distance between d3 may be substantially zero, or even zero, for example, when the first spacer element and the second spacer element 400a, 400b form a joint point in the crotch region and connect to each other.

Figure 8:
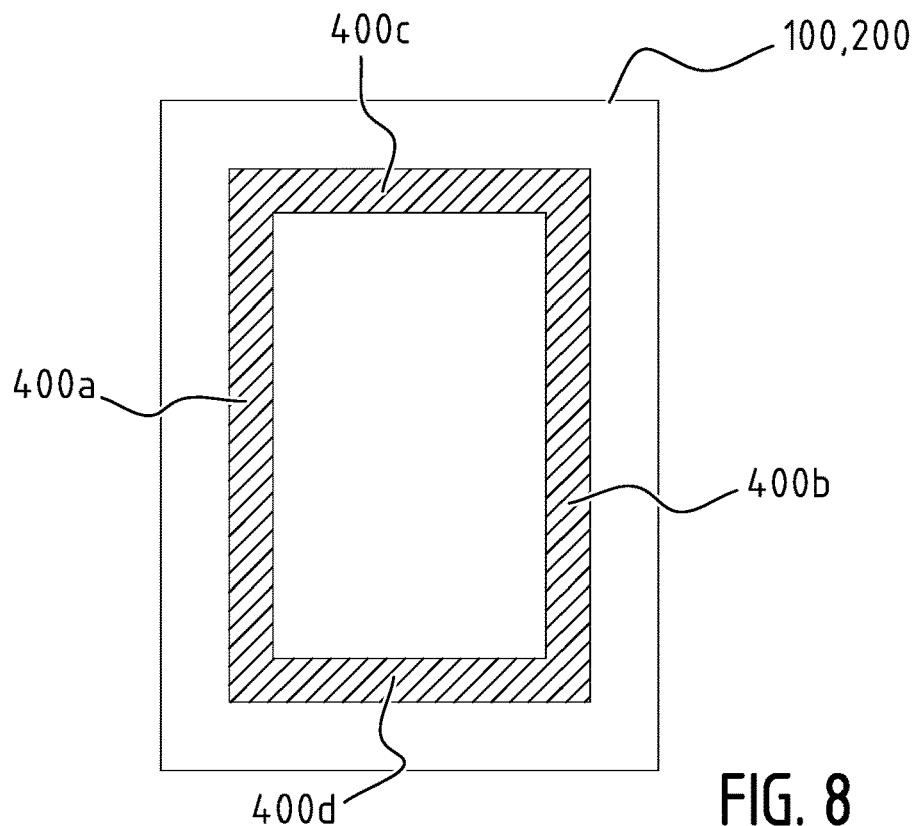

FIG. 8 illustrates another exemplary embodiment of an absorbent article comprising a spacer element 400 which form an enclosed region. The absorbent article comprises a liquid pervious topsheet 100, a liquid impervious backsheet 200, and an absorbent material between the topsheet 100 and the backsheet 200. A first spacer element 400a, a second spacer element 400b, a third spacer element 400c, and a fourth spacer element 400d of an elongated shape are included between the topsheet 100 and the backsheet 200, as in FIGS. 3A-3C. Alternatively a core wrap may be provided as in the embodiment of FIG. 4. The spacer elements 400a, 400b may have similar properties as described above for other embodiments with one or two spacer elements. The first spacer element 400a and the second spacer element 400b may have substantially the same length and width, and may be substantially parallel and run in the longitudinal direction of absorbent article. The third spacer element 400c and the fourth spacer element 400d may also have substantially the same length and width, and may be substantially parallel and run in the transverse direction of absorbent article. The front end of the first spacer element 400a connects to the left end of the third spacer element 400c, and the rear end of the first spacer element 400a connects to the left end of the fourth spacer element 400d. The front end of the second spacer element 400b connects to the right end of the third spacer element 400c, and the rear end of the second spacer element 400b connects to the right end of the fourth spacer element 400d. Together, they form an enclosed region which has a substantially rectangular shaped. In other embodiments, the enclosed region may also have a substantially "O" shaped region, or a substantially polygon shaped region, a substantially triangular shaped region, a diamond shaped region, a substantially hexagonal shaped region, or any other shape. In that manner liquid can be distributed around the boundary of the enclosed region, such that it can be absorbed from the entire boundary by the absorbent material in the enclosed region and by the absorbent material in a region surrounding the enclosed region.

Figure 9:
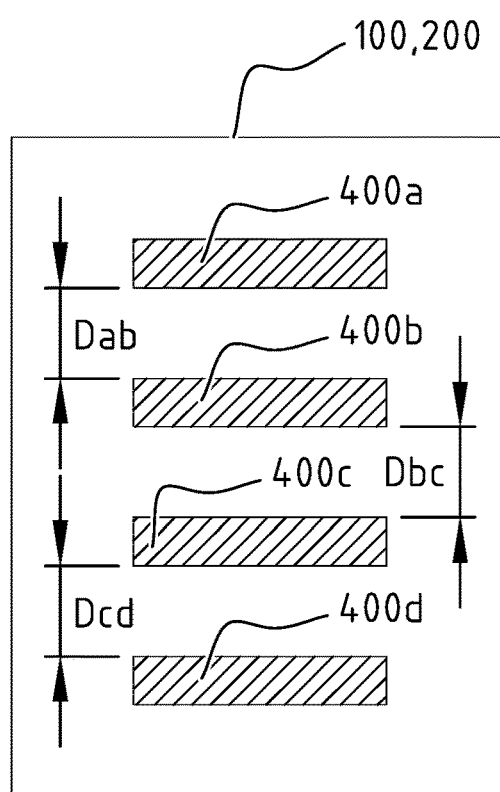

FIG. 9 illustrates another exemplary embodiment of an absorbent article comprising a plurality of transverse spacer elements 400a, 400b, 400c, 400d. The absorbent article comprises a liquid pervious topsheet 100, a liquid impervious backsheet 200, and an absorbent material between the topsheet 100 and the backsheet 200. A first spacer element 400a, a second spacer element 400b, a third spacer element 400c, and a fourth spacer element 400d of an elongated shape is included between the topsheet 100 and the backsheet 200, as in FIGS. 3A-3C. Alternatively a core wrap may be provided as in the embodiment of FIG. 4. The spacer elements 400a, 400b may have similar properties as described above for other embodiments with one or two spacer elements. The first spacer element 400a, the second spacer element 400b, the third spacer element 400c, and the fourth spacer element 400d extend from the first longitudinal portion of the absorbent article to the second longitudinal portion of the absorbent article and are substantially parallel and run in the transverse direction of absorbent article. The spacer elements 400a, 400b, 400c, 400d may have substantially the same length in the transverse direction and the same width in the longitudinal direction of the absorbent article. However, it is also possible that they may have a different length and/or width. For example, the spacer elements in the front portion of the absorbent article may be longer and/or wider, compared to the spacer elements in the rear portion of the absorbent article. The distance between each part of the neighboring spacer elements in the longitudinal direction of the absorbent article Dab, Dbc, Dcd may substantially be the same, preferably the distance is at least 5 mm, more preferably at least 10 mm. However, the distance between each part of the neighboring spacer elements in the longitudinal direction of the absorbent article may also be different, for example, the spacer elements in the front portion of the absorbent article may be closer to each other compared to the spacer elements in the rear portion of the absorbent article. This embodiment has the advantage that the liquid distribution and communication in a transverse direction, between the left and right portion of the absorbent article is further improved.

Figure 10:
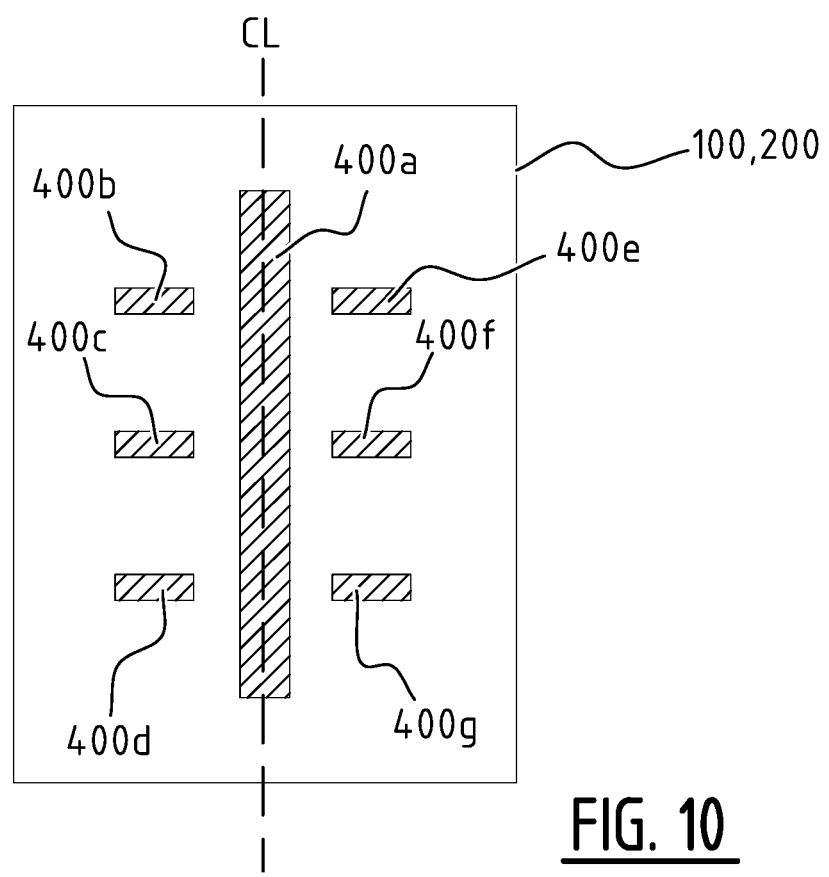

FIG. 10 illustrates another exemplary embodiment of an absorbent article comprising a longitudinal spacer element 400a and a plurality of transverse spacer elements 400b. The absorbent article comprises a liquid pervious topsheet 100, a liquid impervious backsheet 200, and an absorbent material between the topsheet 100 and the backsheet 200. A first spacer element 400a, a second spacer element 400b, a third spacer element 400c, a fourth spacer element 400d, a fifth spacer element 400e, a sixth spacer element 400f, and a seventh spacer element 400g are included between the topsheet 100 and the backsheet 200, e.g. as in FIGS. 3A-3C. Alternatively a core wrap may be provided as in the embodiment of FIG. 4. The spacer elements 400a, 400b may have similar properties as described above for other embodiments with one or two spacer elements. The first spacer element 400a extends in the longitudinal direction of absorbent article, from the crotch region to the front and rear edge of the absorbent article, preferably located on the longitudinal center line CL of the absorbent article. The second to the seventh spacer elements 400b, 400c, 400d, 400e, 400f, 400g may have substantially the same length, which is shorter than the length of the first spacer element, and they may run in the transverse direction of the absorbent article. For example, the second to the fourth spacer elements 400b, 400c, 400d are located on the left portion of the absorbent article and are substantially parallel, and the fifth to the seventh spacer elements 400e, 400f, 400g are located on the right portion of the absorbent article and are also substantially parallel. The first spacer element 400a may be permanently attached to the topsheet 100 and/or the backsheet 200, and there may be substantially no absorbent material between the first spacer element and the topsheet and between the first spacer element and the backsheet.

Alternatively, if a core wrap is present, the first spacer element 400a may be permanently attached to the top core wrap sheet and/or the back core wrap sheet, and there may be substantially no absorbent material between the first spacer element and the top core wrap sheet and between the first spacer element and the back core backsheet. Meanwhile the second to the seventh spacer elements 400b, 400c, 400d, 400e, 400f, 400g may be semi-permanently attached to the topsheet 100 and/or the backsheet 200 (or if a core wrap is present, to the core wrap), such that the attachment loosens upon wetting. In that way temporary transverse channels are created which disappear as the absorbent material starts swelling. There may be substantially no absorbent material between the second to the seventh spacer elements and the topsheet (or top core wrap sheet) and between the second to the seventh spacer elements and the backsheet (or back core wrap sheet), but it is also possible to have some absorbent material above and/or below the second to seventh spacer elements. Seen in a cross-section view, the spacer elements 400a, 400b, 400c, 400d, 400e, 400f, 400g may have a different thickness. For example, the first spacer element 400a may be thicker than the second to the seventh spacer elements 400b, 400c, 400d, 400e, 400f, 400g.

A skilled person understands that other embodiments may be envisaged combining a spacer element which attaches to the topsheet and/or the backsheet (or to the core wrap), and a spacer element which does not attach to the topsheet and/or the backsheet (or to the core wrap), and/or combining a spacer element running in the transverse direction and a spacer element running in the longitudinal direction of the absorbent article.

It is clear to the skilled person, that the different arrangements of spacer elements may be applied to both absorbent articles comprising an absorbent core (e.g. the embodiment of FIGS. 2A and 2B), and absorbent articles which do not comprise an independent absorbent core (e.g. embodiment of FIGS. 1A and 1B or of FIGS. 3A-3C).

The skilled person also understands that the principles of the absorbent article comprising spacer elements can also be used in an absorbent core.

Figure 11:
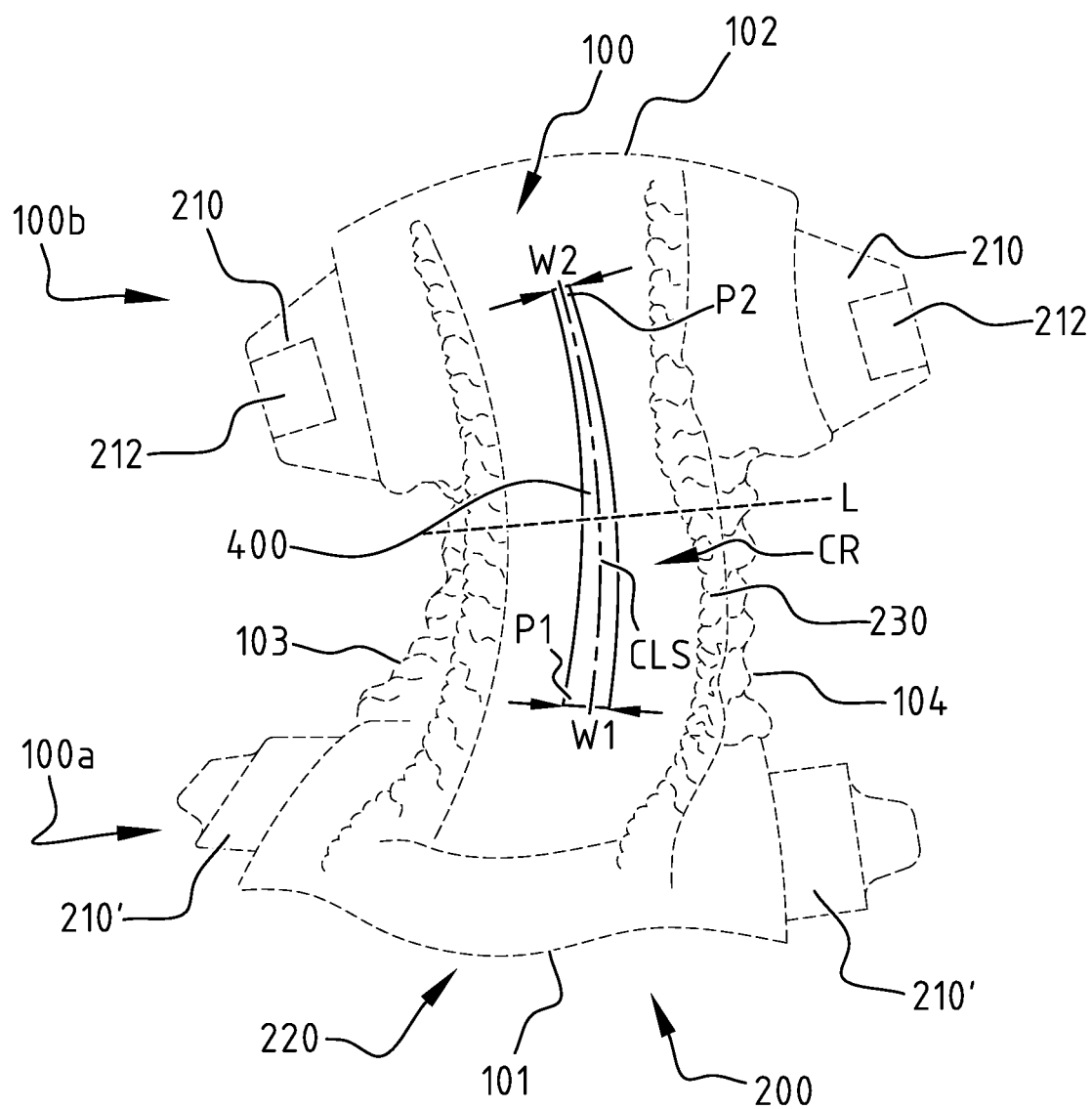
FIG. 11 is a schematic perspective view of an exemplary embodiment of a diaper.

FIG. 11 illustrates in more detail an embodiment of a diaper. The chassis of the diaper in FIG. 11 comprises a liquid pervious topsheet 100 and liquid impervious backsheet 200. Preferably the chassis further includes side panels or ears 210, elasticized leg cuffs 230 and elastic waist elements (not shown). A front end portion of diaper is configured as a front waist region 100a. The opposite rear end portion is configured as a back waist region 100b of the diaper. An intermediate portion of the diaper is configured as crotch region CR, which extends longitudinally between first and second waist regions 100a and 100b. Waist regions 100a and 100b may include elastic waist elements such that they gather about the waist of the wearer to provide improved fit and containment. Crotch region CR is that portion of the diaper which, when the diaper is worn, is generally positioned between the wearer's legs. The periphery of diaper is defined by the outer edges of the diaper in which longitudinal edges 103, 104 run generally parallel to a longitudinal axis of diaper and transverse end edges 101, 102 run between the longitudinal edges 103, 104 generally parallel to a transverse axis of diaper. The chassis also comprises a fastening system, which may include at least one fastening or securing member 212 and at least one landing zone 220. The various components within diaper may be bound, joined or secured by any method known in the art, for example by adhesives in uniform continuous layers, patterned layers or arrays of separate lines, spirals or spots. As explained in connection with the embodiments of the previous figures, optionally a core wrap may be provided. Optional top core wrap sheet, topsheet, optional back core wrap sheet, backsheet, absorbent material and other components may be assembled in a variety of well-known configurations and are well known in the art.

Backsheet 200 covers absorbent material and preferably extends toward longitudinal edges 103, 104 and front and rear edges 101, 102 of the diaper and may be joined with top sheet 100. Backsheet 200 prevents bodily exudates absorbed by the absorbent material and contained within diaper from soiling other external articles that may contact the wearer, such as bed sheets and undergarments. In preferred embodiments, backsheet 200 is substantially impervious to bodily exudates and comprises a laminate of a nonwoven and a thin plastic film such as a thermoplastic film. Backsheet may comprise breathable materials that permit vapor to escape from diaper while still preventing bodily exudates from passing through backsheet. It may be semi-rigid, non-elastic and can be made fully or partially elasticized and include backing.

The topsheet 100 which is located above the absorbent material, is preferably soft, exhibits good strikethroughs and has a reduced tendency to rewet from the liquid absorbent material. Top sheet may be semi-rigid and non-elastic, or may be fully or partially elasticized. Topsheet 100 is intended to be placed in close proximity to the skin of the wearer when the diaper is worn. Topsheet 100 permits bodily exudates to rapidly penetrate it so as to flow more quickly toward the absorbent material via a top surface thereof and via one or more channels created as a consequence of the presence of one or more spacer elements 400, preferably not allowing such bodily exudates to flow back through topsheet 100.

In the embodiment of FIG. 11 one spacer element 400 is shown, but there may be provided more than one spacer element as described above in connection with the other figures. The spacer element 400 has a first width (w1) at a first position (P1) and a second width (w2) at a second position (P2). The first width w1 may be the same of different from the second width w2. The first width may be larger than the second width w2, and the width of the spacer element may increase from the second position P2 to the first position P1. The width of the spacer element 400 is measured perpendicularly to a center line CLs of the spacer element 400. The center line CLs is a line which is at the same distance of opposite edges of the first spacer element 400. Preferably the opposite edges extend in a length direction of the spacer element 400. In this embodiment the center line CLs is a straight line. In other embodiments, the center line CLs may be a curve, or a polyline, etc.

Topsheet 100 may be constructed from any one of a wide range of liquid and vapor permeable, preferably hydrophilic, materials. The upper and lower surface of topsheet 100 may be treated differently. Topsheet 100 may include e.g. a surfactant on the upper surface so as to facilitate liquid transfer there through, especially at a central zone or area of topsheet located over the absorbent material, and/or a hydrophobic agent on the lower surface to minimize the liquid contained within absorbent material from contact wetting topsheet 100 thereby reducing rewet values. Topsheet 100 may be coated with a substance having rash preventing or rash reducing properties. Preferably, topsheet 100 covers substantially the entire wearer facing area of diaper, including substantially all of front waist region 100a, back waist region 100b, and crotch region CR. Optionally, side panels 210, 210' and/or waist feature layers of the inner region may be formed from the same single topsheet material. Alternatively, topsheet may be formed from multiple different materials which vary across of topsheet. Such a multiple piece design allows for creation of preferred properties and different zones of the topsheet 100.

The absorbent material may comprise any absorbent material that is generally compressible, conformable, non-irritating to the wearer's skin, and capable of absorbing and retaining bodily exudates. Preferably, the absorbent material comprises fluff material, typically cellulosic fluff pulp. However, in other embodiments, the absorbent material may be substantially fluffless and comprise superabsorbent polymers. Also, the absorbent material may comprise a combination of cellulosic fluff pulp and superabsorbent polymers. The absorbent material extend over substantially the full length and/or width of diaper. However, as in the embodiment of FIGS. 2A-2B and 3A-3C, preferably the absorbent material is not coextensive with the entire diaper and is limited to certain regions of diaper including the crotch region CR. In various embodiments, the absorbent material extends more or less to the edges of diaper but the absorbent material is concentrated in the crotch region CR or another target zone of the diaper and does not extend over the full length. In FIGS. 2A-2B, the absorbent core 300 is shown as having a substantially rectangular configuration, however, absorbent core 300 may be shaped differently, such as, elliptical, dogbane shaped, T-shaped or I-shaped. In FIGS. 3A-3C, the area covered by absorbent material is substantially rectangular, but also this area may be shaped differently, such as, elliptical, dogbane shaped, T-shaped or I-shaped. More in particular the width of a front portion of the absorbent core or area where absorbent materials is present may be smaller than the width of a rear portion of the absorbent core or area where absorbent materials is present.

Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers. Superabsorbent polymers are water-swellable, water-insoluble organic or inorganic materials capable of absorbing at least about 20 times its weight and in an aqueous solution containing 0.9 weight percent of sodium chloride.

Diaper may also utilize a pair of containment walls or cuffs 230. Each cuff 230 is a longitudinally extending wall structure preferably positioned on each side of absorbent material and spaced laterally from the center line CL.

Preferably, cuffs 230 are attached, for example, by adhesive or sonic bonding to the lower structure. Preferably, cuffs 230 are equipped with elastic members. When released or otherwise allowed relaxing, the elastic members retract inwardly. When diaper is worn, the elastic members function to contract cuffs 230 about the buttocks and the thighs of the wearer in a manner, which forms a seal between diaper, the buttocks and the thighs.

The waist regions 100a and 100b each comprise a central region and a pair of side panels or ears 210, 210' which typically comprise the outer lateral portions of the waist regions. These side panels 210, 210' may be unitary with the chassis or may be attached or joined thereto by any means know in the art. Preferably, the side panels 210 positioned in the back waist region 100b are flexible, extensible and/or elastic in at least the lateral direction. In another embodiment the side panels 210 are non-elastic, semi-rigid, rigid and/or stiff. In order to keep diaper in place about the wearer, preferably at least a portion of the back waist region 100b is attached by fastening or securing members 212 to at least a portion of the front waist region 100a. The fastening or securing members 212 may be e.g. adhesive, mechanical fasteners, hook and loop features, conceivable strings and/or combinations thereof. The fastening or securing members 212 may also be co-adhesive such that they adhere to each other but not other materials. Preferably the materials making up the fastening or securing members 212 are flexible, extensible and/or elastic, allowing them to better conform to the shape and movements of the body and thus, to reduce the likelihood that the fastening system will irritate or injure the wearer's skin. Alternatively, the absorbent article may be pants and the like. In this configuration, the absorbent article may or may not have fastening members.

Diaper may also employ additional layers, such as an acquisition layer and/or dispersion layer situated between topsheet and absorbent material, and/or coverstock layers, and/or other layers situated between absorbent material and backsheet. An acquisition layer and/or dispersion layer serves to slow down the flow so that the liquid has adequate time to be absorbed by absorbent material.

Diaper may also include such other features, components and elements as are known in the art including waistbands, waist cap features, elastics and the like to provide better fit, containment and aesthetic characteristics. These features may be assembled in a variety of well-known configurations and are well known in the art.

The invention claimed is:

1. An absorbent article having a front edge intended to be positioned at a front side of a person and a rear edge intended to be positioned at a rear side of a person, said absorbent article comprising a liquid pervious topsheet, a liquid impervious backsheet, and an absorbent material between said topsheet and said backsheet, wherein at least a first spacer element is included between said topsheet and said backsheet, wherein the first spacer element has a top side facing the topsheet, a bottom side facing the backsheet, and a number of lateral sides between the top and the bottom side;
    said first spacer element being configured to guide liquid to the absorbent material upon wetting of the absorbent article;
    wherein no absorbent material is present between the first spacer element and the topsheet; and
    wherein the first spacer element is attached to both the topsheet and the backsheet;
    wherein said attachment is realized by any of the following: a binder layer from glue, an ultrasonic bond, a heat bond, a pressure bond, or combinations thereof,
    wherein the absorbent material extends along the lateral sides of the first spacer element such that a contour of the first spacer element is adjacent to and surrounded by the absorbent material as seen from a top view and such that a valley is created at a location of the first spacer element by the absorbent material that expands in volume upon wetting of the article while the first spacer element remains attached to both the topsheet and the backsheet.

2. The absorbent article according to claim 1, wherein an entirety of the first spacer element is liquid impervious.

3. The absorbent article according to claim 1, wherein the first spacer element has at least an outer surface which is liquid-impervious and wherein said outer surface is attached to the topsheet and/or backsheet via by any of the following: the ultrasonic bond, the heat bond, the pressure bond, or combinations thereof.

4. The absorbent article according to claim 1, wherein the first spacer element is made of a material configured to absorb no or less liquid than the absorbent material;
    and/or wherein the first spacer element configured to absorb no or less liquid than a same volume of the absorbent material.

5. The absorbent article according to claim 1, wherein the first spacer element is an elongated element that is lengthened more in a longitudinal direction of the absorbent article than in a latitudinal direction, such that an elongated channel is formed upon wetting.

6. The absorbent article according to claim 1, wherein the absorbent article has a crotch region in between the front edge and the rear edge;
    wherein the first spacer element extends from the crotch region in the direction of the front and/or rear edge.

7. The absorbent article according to claim 1, wherein the first spacer element extends in a longitudinal direction of the absorbent article.

8. The absorbent article according to claim 1, wherein the absorbent material is part of an absorbent core comprising a top core wrap sheet and a back core wrap sheet with the absorbent material positioned in between the top core wrap sheet and the back core wrap sheet and wherein the first spacer element is attached to the top core wrap sheet and the back core wrap sheet.

9. The absorbent article according to claim 1, wherein the first spacer element is made of any one of the following materials: a non-water-absorbing polymer material, fibers, wherein optionally the materials are chemically and/or mechanically treated.

10. The absorbent article according to claim 1, wherein the absorbent article has a length between the front edge and the rear edge; wherein the first spacer element has a length which is at least 5% of the length of the absorbent article.

11. The absorbent article according to claim 1, wherein the absorbent article has a transverse crotch line (L) dividing the absorbent core in a front portion and a rear portion on either side of the transverse crotch line (L), wherein the first spacer element extends in the front portion and in the rear portion.

12. The absorbent article according to claim 1, wherein substantially no absorbent material is present between the first spacer element and the topsheet and between the first spacer element and the backsheet; and/or
    wherein said first spacer element extends, seen in the transverse direction of the absorbent article, over a transverse distance which is at least 1 mm; and/or wherein said first spacer element extends, seen in the thickness direction of the absorbent article, over a distance which is at least 1 mm; and/or wherein the absorbent material comprises cellulosic fluff pulp and/or superabsorbent particles.

13. The absorbent article according to claim 1, wherein a binder layer attaches the spacer element to the topsheet and wherein a further binder layer attaches the spacer element to the backsheet.

14. The absorbent article according to claim 1, further comprising a second spacer element between the topsheet and the backsheet, wherein the first spacer element and the second spacer element are an elongated elements and are diverging outwardly in a direction of the front edge and wherein the absorbent article has a longitudinal center line dividing the absorbent article in a first longitudinal portion and a second longitudinal portion on either side of the longitudinal center line and the first spacer element and the second spacer element are extended symmetrically with respect to a longitudinal center line.

15. The absorbent article according to claim 14, wherein any one or more of the following features is present:
   the second spacer element extends in the front portion and in the rear portion;
   the absorbent article has a transverse crotch line dividing the absorbent core in a front portion and a rear portion on either side of the transverse crotch line-, said absorbent article further comprising a third spacer element between the topsheet and the backsheet; wherein the first and second spacer element extend at least in the front portion and the third spacer element extends at least in the rear portion, optionally further comprising a fourth spacer element between the topsheet and the backsheet; wherein the fourth spacer element extends at least in the rear portion, wherein preferably the third and the fourth spacer element are arranged symmetrically with respect to a longitudinal center line of the absorbent article; wherein optionally a maximum distance between the first and the second spacer element is different from a maximum distance between the third and the fourth spacer element;
   the first and the second spacer element diverge in a direction of the front edge and/or the rear edge;
   the first and second spacer element together form a substantially X-shaped zone;
   a maximum distance between the first and the second spacer element is between 5 and 70% of the width of the absorbent article; or
   the length of the first and second spacer is larger than 10% of the length of the absorbent article.

16. An absorbent article having a front edge intended to be positioned at a front side of a person and a rear edge intended to be positioned at a rear side of a person, said absorbent article comprising a liquid pervious topsheet, a liquid impervious backsheet and an absorbent material between said topsheet and said backsheet, wherein at least a first spacer element is included between said topsheet and said backsheet, said first spacer element being configured to guide liquid to the absorbent material via a valley created at a location of the first spacer element upon wetting of the absorbent article;

wherein seen in a transverse direction of the absorbent article, the first spacer element extends over a distance w which is at least 2 mm and smaller than 20 mm;

wherein the first spacer element has a top side facing the topsheet, a bottom side facing the backsheet, and lateral sides between the top and the bottom side, and wherein the absorbent material extends along the lateral sides of the first spacer element such that a contour of the spacer element is adjacent to and surrounded by the absorbent material as seen from a top view;

wherein the spacer element is made of a non-water-absorbing polymer material; and wherein the first spacer element has an outer surface which is liquid-impervious such that the first spacer element absorbs no liquid.

17. The absorbent article according to claim 16, wherein absorbent material is present between the top side of the spacer element and the topsheet and between the bottom side of the spacer element and the backsheet and wherein the spacer element is attached to the absorbent material above and below.

18. An absorbent article having a front edge intended to be positioned at a front side of a person and a rear edge intended to be positioned at a rear side of a person, said absorbent article comprising a liquid pervious topsheet, a liquid impervious backsheet and an absorbent material between said topsheet and said backsheet, wherein at least a first spacer element is included between said topsheet and said backsheet, said first spacer element being configured to guide liquid to the absorbent material upon wetting of the absorbent article;

wherein the absorbent material is part of an absorbent core comprising a top core wrap sheet and a back core wrap sheet with the absorbent material positioned in between the top core wrap sheet and the bottom core wrap sheet;

wherein the first spacer element is attached to the top core wrap sheet and/or to the back core wrap sheet such that a valley is created at the location of the first spacer element upon wetting of the absorbent article, wherein said attachment of the spacer element to the top core and/or to the back core wrap sheet is realized by any of the following: a binder layer from glue, an ultrasonic bond, a heat bond, a pressure bond, or combinations thereof;

wherein the first spacer element has a top side facing the topsheet, a bottom side facing the backsheet, and lateral sides between the top and the bottom side, and wherein the absorbent material extends along the lateral sides of the first spacer element such that a contour of the spacer element is adjacent to and surrounded by the absorbent material as seen from a top view;

wherein said first spacer element extends, seen in the thickness direction of the absorbent article, over a distance which is at least 0.5 mm.

19. The absorbent article according to claim 18, wherein a binder layer attaches the spacer element to the top core wrap sheet and wherein a further binder layer attaches the spacer element to the back core wrap sheet.

20. The absorbent article according to claim 18, wherein an entirety of the spacer element is liquid impervious.

* * * * *